(12) United States Patent
Schaeffer et al.

(10) Patent No.: US 9,457,173 B2
(45) Date of Patent: Oct. 4, 2016

(54) METHODS OF PROVIDING ACCESS TO A SALIVARY DUCT

(75) Inventors: Darin Schaeffer, Bloomington, IN (US); Kathryn Evert, Bloomington, IN (US); Thomas Cherry, Covington, LA (US); Jack Kolenda, Oakville (CA)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 745 days.

(21) Appl. No.: 13/607,861

(22) Filed: Sep. 10, 2012

(65) Prior Publication Data

US 2013/0245662 A1  Sep. 19, 2013

Related U.S. Application Data

(60) Provisional application No. 61/533,192, filed on Sep. 10, 2011.

(51) Int. Cl.
*A61M 29/02* (2006.01)
*A61M 25/06* (2006.01)

(52) U.S. Cl.
CPC ...... *A61M 29/02* (2013.01); *A61M 2025/0681* (2013.01)

(58) Field of Classification Search
CPC ..................... A61M 2025/0691; A61M 29/02
See application file for complete search history.

(56) References Cited

U.S. PATENT DOCUMENTS

| | | | |
|---|---|---|---|
| 5,653,230 A | 8/1997 | Ciaglia et al. | |
| 6,206,870 B1 | 3/2001 | Kanner | |
| 7,361,168 B2 | 4/2008 | Makower et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,559,925 B2 * | 7/2009 | Goldfarb ............ | A61B 1/00126 604/510 |
| 7,645,272 B2 * | 1/2010 | Chang ................. | A61F 11/002 604/509 |
| 7,654,997 B2 | 2/2010 | Makower et al. | |
| 7,678,099 B2 | 3/2010 | Ressemann et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,740,642 B2 | 6/2010 | Becker | |

(Continued)

FOREIGN PATENT DOCUMENTS

| | | |
|---|---|---|
| EP | 2478929 | 7/2012 |
| EP | 2522386 | 11/2012 |

(Continued)

OTHER PUBLICATIONS

Geisthoff, Urban W., Basic Sialendoscopy Techniques, Otolaryngol Clin N Am, 2009, p. 1029-1052, vol. 42, Elsevier Inc.

(Continued)

*Primary Examiner* — Julie A Szpira
(74) *Attorney, Agent, or Firm* — Buchanan Nipper

(57) ABSTRACT

Methods of treatment are described. More particularly, methods of providing access to a bodily passage, such as a salivary duct, are described herein. For example, methods of providing access to a salivary duct and introducing a sheath and wire guide are described herein. In addition, various methods of treatment are described herein. For example, methods of treating a stone located within a salivary duct are described herein.

20 Claims, 9 Drawing Sheets

(56) References Cited

U.S. PATENT DOCUMENTS

| | | | |
|---|---|---|---|
| 7,753,929 B2 * | 7/2010 | Becker | A61M 25/10 606/196 |
| 7,753,930 B2 | 7/2010 | Becker | |
| 7,771,409 B2 | 8/2010 | Chang et al. | |
| 7,803,150 B2 | 9/2010 | Chang et al. | |
| 7,854,744 B2 | 12/2010 | Becker | |
| 7,879,061 B2 | 2/2011 | Keith et al. | |
| 7,918,871 B2 | 4/2011 | Truitt et al. | |
| 8,088,101 B2 | 1/2012 | Chang et al. | |
| 8,090,433 B2 | 1/2012 | Makower et al. | |
| 8,100,933 B2 | 1/2012 | Becker | |
| 8,114,062 B2 | 2/2012 | Muni et al. | |
| 8,123,722 B2 | 2/2012 | Chang et al. | |
| 8,142,422 B2 | 3/2012 | Makower et al. | |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,317,816 B2 | 11/2012 | Becker | |
| 8,388,642 B2 | 3/2013 | Muni et al. | |
| 8,414,473 B2 | 4/2013 | Jenkins et al. | |
| 8,424,534 B2 | 4/2013 | Lyons et al. | |
| 8,425,457 B2 | 4/2013 | John et al. | |
| 8,435,290 B2 | 5/2013 | Clifford et al. | |
| 8,491,620 B2 * | 7/2013 | Brasington | A61M 29/02 606/192 |
| 8,899,225 B2 | 12/2014 | Bosel | |
| 8,911,399 B2 | 12/2014 | Boatman | |
| 9,192,747 B2 | 11/2015 | Hardert | |
| 2007/0129751 A1 | 6/2007 | Muni et al. | |
| 2007/0167682 A1 | 7/2007 | Goldfarb et al. | |
| 2007/0208252 A1 | 9/2007 | Makower | |
| 2007/0293727 A1 | 12/2007 | Goldfarb et al. | |
| 2008/0015472 A1 | 1/2008 | Ressemann et al. | |
| 2008/0015544 A1 | 1/2008 | Keith et al. | |
| 2008/0097515 A1 * | 4/2008 | Chang | A61F 11/002 606/196 |
| 2008/0103521 A1 | 5/2008 | Makower et al. | |
| 2008/0119693 A1 | 5/2008 | Makower et al. | |
| 2008/0132938 A1 | 6/2008 | Chang et al. | |
| 2008/0172033 A1 | 7/2008 | Keith et al. | |
| 2008/0195041 A1 | 8/2008 | Goldfarb et al. | |
| 2008/0215036 A1 * | 9/2008 | Vogel | A61B 17/12131 604/514 |
| 2008/0228085 A1 | 9/2008 | Jenkins et al. | |
| 2008/0275483 A1 | 11/2008 | Makower et al. | |
| 2008/0287908 A1 | 11/2008 | Muni et al. | |
| 2008/0319424 A1 | 12/2008 | Muni et al. | |
| 2009/0030274 A1 | 1/2009 | Goldfarb et al. | |
| 2009/0187098 A1 | 7/2009 | Makower et al. | |
| 2009/0198216 A1 | 8/2009 | Muni et al. | |
| 2009/0216196 A1 | 8/2009 | Drontle et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2010/0030113 A1 | 2/2010 | Morriss et al. | |
| 2010/0042046 A1 | 2/2010 | Chang et al. | |
| 2010/0076269 A1 | 3/2010 | Makower et al. | |
| 2010/0114066 A1 | 5/2010 | Makower et al. | |
| 2010/0168511 A1 | 7/2010 | Muni et al. | |
| 2010/0174138 A1 | 7/2010 | Chang et al. | |
| 2010/0174308 A1 | 7/2010 | Chang et al. | |
| 2010/0198191 A1 | 8/2010 | Clifford et al. | |
| 2010/0198247 A1 * | 8/2010 | Chang | A61F 11/002 606/185 |
| 2010/0211007 A1 | 8/2010 | Lesch, Jr. et al. | |
| 2010/0268245 A1 * | 10/2010 | Chang | A61F 11/002 606/108 |
| 2010/0274188 A1 | 10/2010 | Chang et al. | |
| 2010/0298862 A1 | 11/2010 | Chang et al. | |
| 2011/0004057 A1 | 1/2011 | Goldfarb et al. | |
| 2011/0060214 A1 | 3/2011 | Makower | |
| 2011/0071349 A1 | 3/2011 | Drontle et al. | |
| 2011/0112512 A1 | 5/2011 | Muni et al. | |
| 2011/0118546 A1 * | 5/2011 | Dillon | A61M 25/0075 600/106 |
| 2011/0160740 A1 | 6/2011 | Makower et al. | |
| 2011/0224652 A1 | 9/2011 | Drontle et al. | |
| 2011/0288477 A1 * | 11/2011 | Ressemann | G06F 17/30516 604/95.04 |
| 2012/0010646 A1 | 1/2012 | Keith et al. | |
| 2012/0071824 A1 | 3/2012 | Chang et al. | |
| 2012/0116254 A1 | 5/2012 | Morriss | |
| 2012/0136207 A1 | 5/2012 | Goldfarb et al. | |
| 2012/0172912 A1 | 7/2012 | Ressemann et al. | |
| 2012/0184983 A1 | 7/2012 | Chang et al. | |
| 2012/0190973 A1 | 7/2012 | Ressemann et al. | |
| 2012/0245419 A1 | 9/2012 | Makower et al. | |
| 2012/0265094 A1 | 10/2012 | Goldfarb et al. | |
| 2012/0283625 A1 | 11/2012 | Keith et al. | |
| 2013/0096605 A1 | 4/2013 | Becker | |

FOREIGN PATENT DOCUMENTS

| | | |
|---|---|---|
| WO | WO03063711 | 8/2003 |
| WO | WO2006020180 | 2/2006 |
| WO | WO2008045242 | 4/2008 |
| WO | WO2011082074 | 7/2011 |
| WO | WO2011084655 | 7/2011 |

OTHER PUBLICATIONS

Australian Patent Office, Patent Examination Report No. 1, Jun. 12, 2013 for Australian patent application No. 2012216740.

RK Ngu et al., Salivary duct strictures: nature and incidence in benign salivary obstruction, Dentomaxillofacial Radiology, The British Institute of Radiology, 2007, vol. 36 pp. 63-67.

N. P. Briffa et al., Use of an embolectomy catheter to remove a submandibular duct stone, British Journal of Surgery, 1989, vol. 76, p. 814.

* cited by examiner

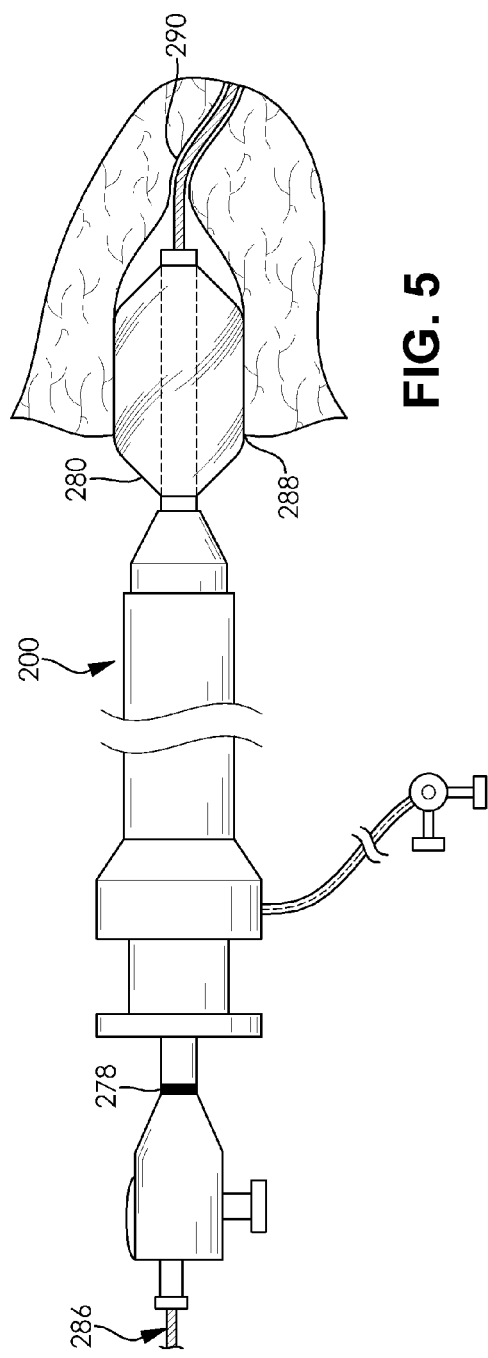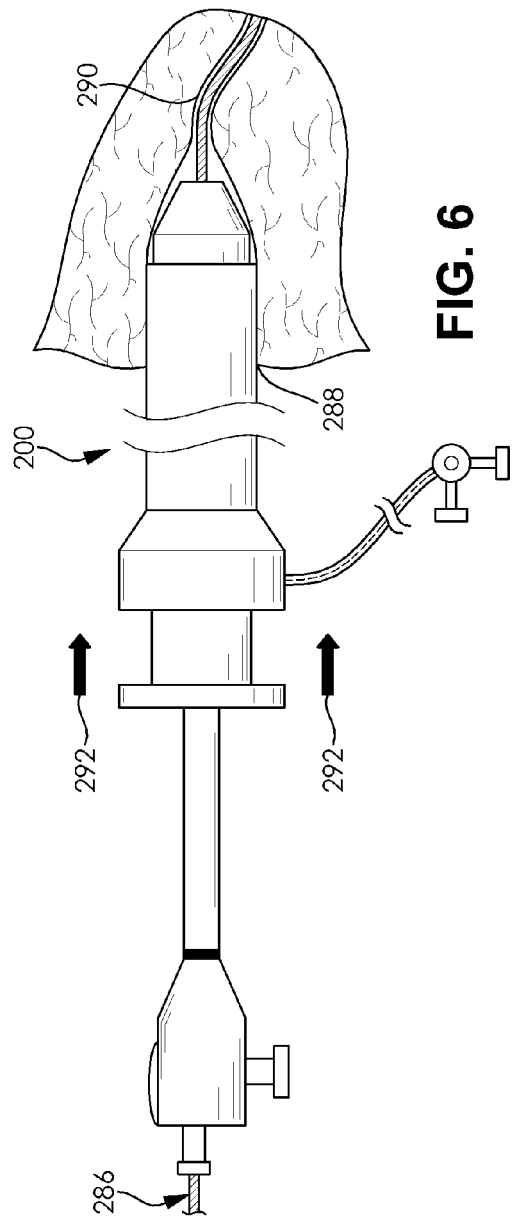

METHODS OF PROVIDING ACCESS TO A SALIVARY DUCT

CROSS REFERENCE TO RELATED APPLICATIONS

This application claims the benefit of U.S. Provisional Application Ser. No. 61/533,192, filed on Sep. 10, 2011. The entire contents of this related application are incorporated into this disclosure by reference.

FIELD

The disclosure relates generally to methods of treatment. Particular embodiments disclosed herein relate to methods of providing access to a bodily passage, such as a salivary duct.

BACKGROUND

The treatment of various medical conditions related to the salivary ducts can involve several techniques, including wire insertion, sheath insertion, balloon dilatation of strictures, irrigant delivery, therapeutic agent delivery, and stone removal. In the salivary duct, each of these procedures is complicated by the size of the salivary duct itself, which is relatively small in comparison to other body vessels within which minimally invasive procedures have become common. Therefore, to perform these techniques, dilation of the papilla and salivary duct is required.

Dilation is currently performed by rotating a metal wire around the wall of the salivary duct and then inserting a tapered metal tool into the papilla. In some instances, sheaths are introduced into a portion of the salivary duct to provide access for one or more treatment devices. However, sheaths having a lumen with a diameter sufficient for the traversal of one or more treatment devices are generally larger than the papilla and at times the salivary duct itself. In addition, the tortuous anatomy of the salivary duct prevents a user from navigating the treatment devices through the salivary duct. Therefore, significant pressure is required to introduce the sheath and/or dilator into the papilla and salivary duct. As a result, the patient is subjected to uncomfortable pressures and damage to the papilla and salivary duct can occur. In instances where a sheath is not used, the repeated access (e.g., introduction and removal) of devices from the salivary duct during diagnosis and treatment increases the likelihood of trauma to the papilla and salivary duct.

Therefore, a need exists for methods of providing access to a bodily passage, such as a salivary duct.

SUMMARY

Several exemplary methods of providing access to a bodily passage, such as a salivary duct, are described herein.

An exemplary method of providing access to a salivary duct having a salivary duct opening comprises a step of inserting a balloon catheter having a proximal end and a distal end into said salivary duct opening such that the distal end is disposed in said salivary duct. The balloon catheter comprising a sheath, an elongate tubular member, and a balloon that is disposed on the elongate tubular member and moveable between a deflated configuration and an inflated configuration. Another step comprises navigating the distal end of the balloon catheter into said salivary duct such that a portion of the balloon is disposed within said salivary duct. Another step comprises passing a fluid into the balloon to move the balloon from the deflated configuration to the inflated configuration and to dilate said salivary duct opening. Another step comprises removing a portion, or the entirety, of the fluid from the balloon. Another step comprises advancing the sheath distally such that a portion of the sheath is disposed within said salivary duct. Another step comprises withdrawing the elongate tubular member from said salivary duct.

Another exemplary method of providing access to a salivary duct having a salivary duct opening comprises a step of inserting a wire guide having a first proximal end and a first distal end into said salivary duct opening such that the first distal end is disposed in said salivary duct. Another step comprises navigating the first distal end of the wire guide towards a point of treatment within said salivary duct. Another step comprises advancing a balloon catheter having a second proximal end and a second distal end over the previously placed wire guide such that the second distal end is disposed in said salivary duct. The balloon catheter comprising a sheath, a dilator, an elongate tubular member, and a balloon that is disposed on the elongate tubular member and moveable between a deflated configuration and an inflated configuration. Another step comprises navigating the second distal end of the balloon catheter into said salivary duct such that a portion of the balloon is disposed within said salivary duct. Another step comprises passing a fluid into the balloon to move the balloon from the deflated configuration to the inflated configuration and to dilate said salivary duct opening. Another step comprises removing a portion, or the entirety, of the fluid from the balloon. Another step comprises advancing the sheath distally such that a portion of the sheath is disposed within said salivary duct. Another step comprises advancing the dilator distally such that a portion of the dilator is disposed within said salivary duct. Another step comprises withdrawing the elongate tubular member from said salivary duct. Another step comprises withdrawing the dilator from said salivary duct.

Another exemplary method of providing access to a salivary duct having a salivary duct opening comprises a step of inserting a wire guide having a first proximal end and a first distal end into said salivary duct opening such that the first distal end is disposed in said salivary duct. Another step comprises navigating the first distal end of the wire guide towards a point of treatment within said salivary duct. Another step comprises advancing a balloon catheter having a second proximal end and a second distal end over the previously placed wire guide such that the second distal end is disposed in said salivary duct. The balloon catheter comprising a sheath, a dilator, an elongate tubular member, and a balloon that is disposed on the elongate tubular member and moveable between a deflated configuration and an inflated configuration. Another step comprises navigating the second distal end of the balloon catheter into said salivary duct such that a portion of the balloon is disposed within said salivary duct. Another step comprises passing a fluid into the balloon to move the balloon from the deflated configuration to the inflated configuration and to dilate said salivary duct opening. Another step comprises removing a portion, or the entirety, of the fluid from the balloon. Another step comprises advancing the sheath distally such that a portion of the sheath is disposed within said salivary duct. Another step comprises advancing the dilator distally such that a portion of the dilator is disposed within said salivary duct. Another step comprises withdrawing the elongate tubular member from said salivary duct. Another step comprises withdrawing the dilator from said salivary duct. The step of advancing the sheath distally such that a portion of the sheath is disposed within said salivary duct is accomplished while the balloon is in the inflated configuration.

Additional understanding of the methods contemplated and/or claimed by the inventors can be gained by reviewing the detailed description of exemplary embodiments, presented below, and the referenced drawings.

BRIEF DESCRIPTION OF THE DRAWINGS

FIG. 5 is a side view of the exemplary balloon catheter illustrated in FIG. 2 having a portion thereof disposed in a salivary duct.

FIG. 6 is a side view of the exemplary balloon catheter illustrated in FIG. 2 having a portion of a sheath and dilator disposed in a salivary duct.

DETAILED DESCRIPTION

The following detailed description and the appended figures are provided to describe and illustrate exemplary embodiments of the invention for the purpose of enabling one of ordinary skill in the relevant art to make and use the invention. The description and drawings are not intended to limit the scope of the invention, or its protection, in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event or circumstance may or may not be present/occur, and that the description includes instances where said element, event or circumstance occurs and instances where it does not. As used herein, the terms "proximal" and "distal" are used to describe opposing axial ends of the particular elements or features being described. The term "bodily passage" refers to any passage within the body of an animal, including, but not limited to, humans, and includes elongate passages. The term "salivary duct" refers to the parotid ducts, submandibular ducts, and/or sublingual ducts. The term "papilla" refers to the projection and opening formed at the end of a salivary duct. The term "attached" refers to the fixed, releasable, or integrated association of two or more elements and/or devices. Thus, the term "attached" includes releasably attaching or fixedly attaching two or more elements.

The term "exemplary" refers to "an example of" and is not intended to convey a meaning of an ideal or preferred embodiment.

Various methods of providing access to a bodily passage are provided. These methods include providing access to a bodily passage, such as a salivary duct. While the methods of providing access to a bodily passage are exemplified by methods of providing access to a salivary duct, the methods can also be used to treat other bodily passages. Furthermore, while the methods described herein are shown and described as a series of acts, it is to be understood and appreciated that the methods are not limited by the order of acts, as some acts may, in accordance with these methods, occur in different orders, and/or concurrently with other acts described herein.

Figure 1:
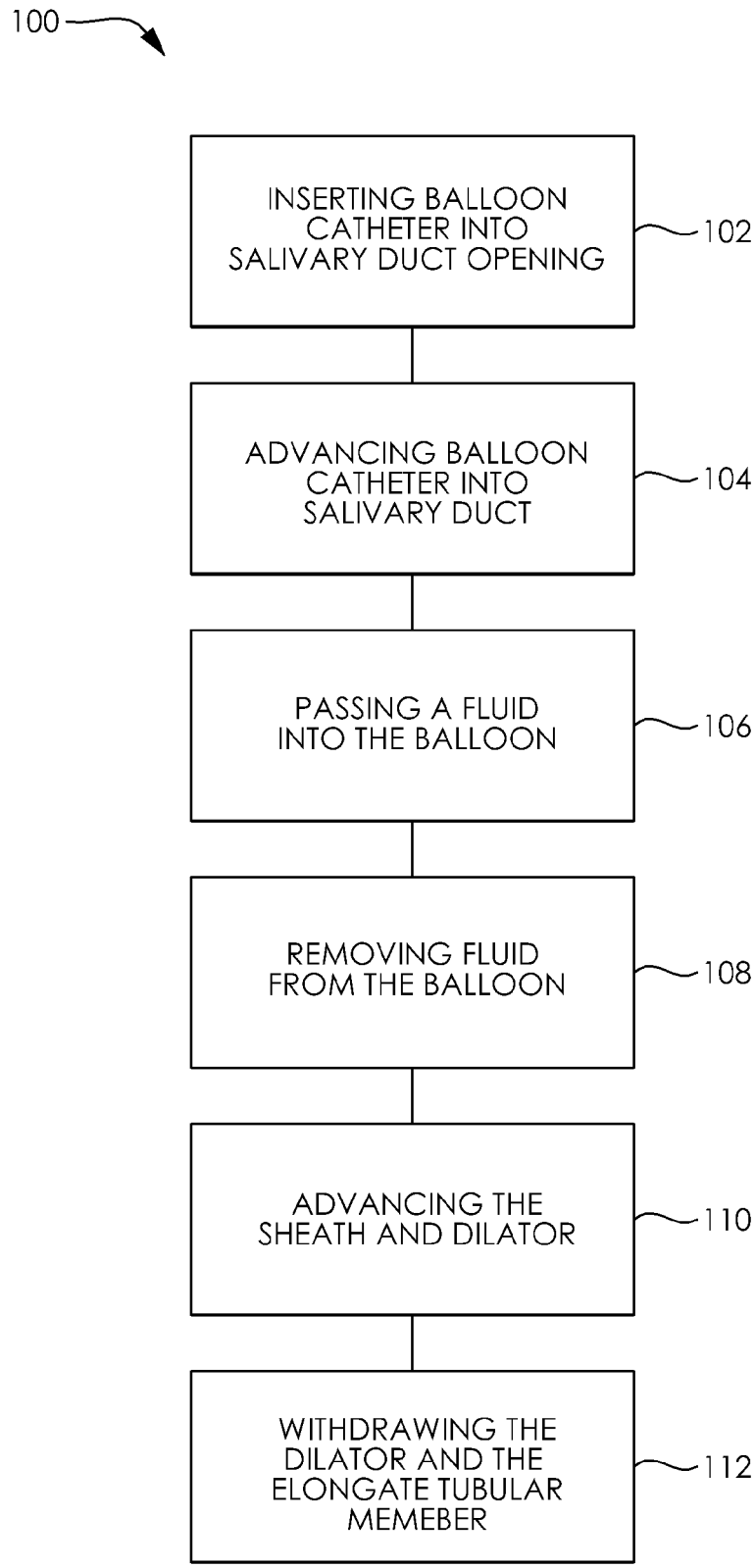
FIG. 1 is a flowchart representation of an exemplary method of treatment.

FIG. 1 is a flowchart representation of an exemplary method 100 of providing access to a salivary duct, having a salivary duct opening, using a balloon. An initial step 102 comprises inserting a balloon catheter having a proximal end and a distal end into a salivary duct opening such that the distal end is disposed past the salivary duct opening and in the salivary duct. The balloon catheter comprises a sheath, a dilator, an elongate tubular member, and a balloon. The sheath has a proximal end and a distal end. The sheath defines a lumen extending between openings located at the proximal end and distal end of the sheath. The dilator is slidably disposed within the lumen of the sheath and has a proximal end, a distal end. The dilator defines a lumen extending between openings located at the proximal end and distal end of the dilator. The elongate tubular member is slidably disposed within the lumen of the dilator. The elongate tubular member has a proximal end and a distal end. The elongate tubular member defines an inflation port, a lumen, an inflation lumen, and an inflation lumen opening. The lumen of the elongate tubular member extends between openings located at the proximal end and the distal end of the elongate tubular member. The inflation lumen of the elongate tubular member extends between an opening in the inflation port and the inflation lumen opening disposed between the proximal end and the distal end of the elongate tubular member. The balloon is disposed on the distal end of the elongate tubular member. The balloon is in communication with the inflation lumen opening, and is moveable between a deflated configuration and an inflated configuration. Another step 104 comprises advancing the distal end of the balloon catheter into the salivary duct such that a portion of the balloon is disposed within the salivary duct. Another step 106 comprises passing a fluid through the inflation lumen and into the balloon to move the balloon from the deflated configuration to the inflated configuration and to dilate the salivary duct opening and the portion of the salivary duct contacting the balloon. Another step 108 comprises removing a portion, or the entirety, of the fluid from the balloon. Another step 110 comprises advancing the sheath and the dilator over the elongate tubular member and balloon such that the distal end of the sheath and the distal end of the dilator are disposed within said salivary duct. Another step 112 comprises withdrawing the dilator and the elongate tubular member from the salivary duct.

The step 102 of inserting a balloon catheter having a proximal end and a distal end into a salivary duct opening such that the distal end is disposed past the salivary duct opening and in a salivary duct can be accomplished by locating an opening of a salivary duct and inserting the distal end of the balloon catheter into the opening of the salivary duct. The opening of the salivary duct can comprise any suitable opening for completing a procedure. Examples of openings considered suitable include, but are not limited to, the papilla, incision (e.g., papillotomy), ductal exploration (e.g., ductal cutdown), and/or sialolithotomy opening. The balloon catheter can comprise any suitable structure for accomplishing the methods described herein. Exemplary balloon catheter structures are described below, but are not intended to be limiting in nature.

Figure 2:
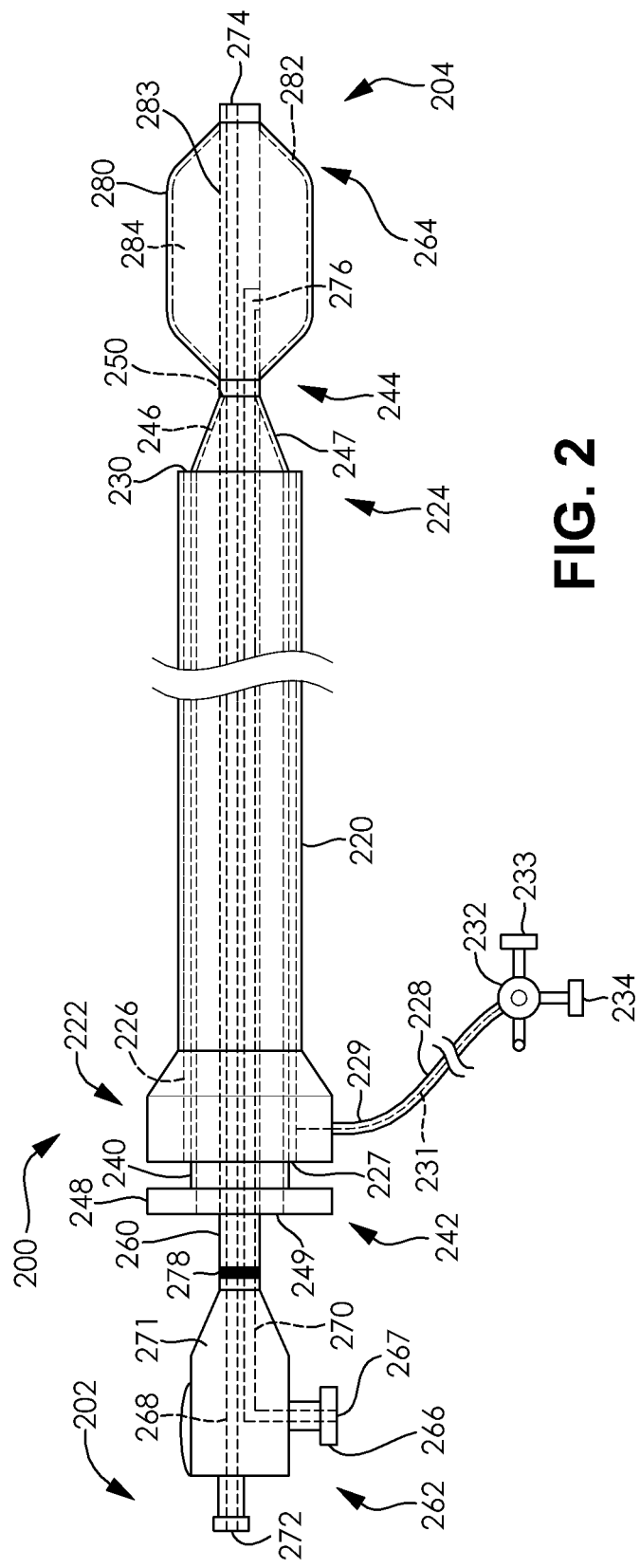
FIG. 2 is a side view of an exemplary balloon catheter.

FIG. 2 illustrates an exemplary balloon catheter 200 comprising a proximal end 202, a distal end 204, a sheath 220, dilator 240, elongate tubular member 260, and a balloon 280.

The sheath 220 comprises a proximal end 222, a distal end 224, and defines a lumen 226 and a side arm 228. The lumen 226 extends between an opening 227 located at the proximal end 222 and an opening 230 located at the distal end 224. The proximal end 222 of the sheath 220 has a greater outside diameter than the remaining portions of the sheath 220, allowing a user to manipulate the sheath 220 during the performance of a procedure (e.g., by applying a proximal or distal force on the proximal end 222 of the sheath 220). Alternatively, the proximal end 222 of the sheath 220 can have an outside diameter that is substantially equal, or equal to, to the remainder of the sheath 220. In a further alternative, a projection (not shown) extending around a portion, or the entirety, of the proximal end 222 of the sheath 220 can be included to allow a user to manipulate the sheath 220 during the performance of a procedure. The side arm 228 comprises a wall 229 that defines a lumen 231 and a valve 232. The lumen 231 is in fluid communication with the lumen 226 of the sheath 220. The side arm 228 advantageously allows for fluid to be evacuated from lumen 226 of the sheath 220 and into lumen 231 through the application of vacuum applied to lumen 231. As excess fluid is introduced through the sheath 220 through an ancillary device, the fluid being pushed up through lumen 226 is evacuated. Alternatively, connector 233 or 234 (e.g., touhy borst connector) maybe used to inject fluid into the sheath to clear the sheath lumen 226 and 231 if needed. The sheath can optionally omit the inclusion of side arm 228. In addition, the sheath 220 can optionally comprise a tapered distal end and a hydrophilic coating to potentially reduce the resistance of insertion and the likelihood of tissue damage.

The sheath 220 is formed of any suitable material (e.g., biocompatible materials, polymeric materials) and can have any suitable size and length. The sheath 220 advantageously provides for lining the salivary duct opening and/or salivary duct to allow for one or more devices to traverse the lumen 226 of the sheath 220 and be inserted and withdrawn from the salivary duct opening and salivary duct. Insertion of the sheath 220 into a bodily passage, such as the salivary duct, is described below. It is considered advantageous to provide a sheath 220 that has a lumen 226 with a diameter configured to allow one or more devices to traverse the length of the sheath 220, or a portion thereof, and provide treatment within the salivary duct (e.g., removal of one or more salivary stones) and/or to a salivary gland. Examples of sheath 220 sizes considered suitable include sheaths 220 in the range from about 1 Fr. to about 20 Fr. The inventors have also determined that sheaths in the range between about 4 Fr. to about 7 Fr. are considered suitable. While particular sheath 220 configurations and sizes have been described, other sheath configurations and sizes are considered suitable, and skilled artisans will be able to select a particular sheath configuration and/or size according to a particular embodiment based on various considerations, such as the size of the salivary duct being treated.

The dilator 240 is slidably disposed within the lumen 226 of the sheath 220 and comprises a proximal end 242, a distal end 244, and defines a lumen 246 and a fitting 248. The lumen 246 of the dilator 240 extends between an opening 249 located at the proximal end 242 and an opening 250 located at the distal end 244. The fitting 248 circumferentially extends around a portion, or the entirety, of the proximal end 242 of the dilator 240 and provides a mechanism for a user to apply a force to the dilator 240 to advance or retract the dilator 240 over the elongate tubular member 260 and within the sheath 220. Optionally, the dilator 240 can omit the inclusion of fitting 248.

The dilator 240 is formed of any suitable material (e.g., biocompatible materials, polymeric materials) and can have any suitable length and outside diameter that allows for the dilator 240 to be slidably disposed within the sheath 220. The distal end 244 of the dilator 240 can optionally comprise a tapered portion 247 that is configured to provide a transition-less, or substantially transition-less, progression between the dilator 240 and the sheath 220. To accomplish a transition-less, or substantially transition-less, configuration the sheath 220 is tapered to a very thin wall at its distal end 224 and the outside diameter of the distal end 244 of the dilator 240 is substantially equal, or equal to, the inside diameter of the sheath 220 such that the transition between the dilator 240 and sheath 220 reduce, or eliminate, the existence of a ledge between the distal end 224 of the sheath 220 and the outside diameter of the dilator 240. Optionally, the dilator 240 can comprise a hydrophilic coating to potentially reduce the resistance of insertion and the likelihood of tissue damage.

The elongate tubular member 260 is slidably disposed within the lumen 246 of the dilator 240 and comprises a proximal end 262, and a distal end 264. The elongate tubular member 260 defines an inflation port 266, a lumen 268, an inflation lumen 270, and a fitting 271. The lumen 268 extends between an opening 272 located at the proximal end 262 and an opening 274 located at the distal end 264. The inflation lumen 270 extends between an opening 267 in the inflation port 266 and an opening 276 located between the proximal end 262 and the distal end 264 of the elongate tubular member 260. The fitting 271 circumferentially extends around a portion, or the entirety, of the proximal end 262 of the elongate tubular member 260 and provides a mechanism for a user to apply a force to the elongate tubular member 260 to advance or retract the elongate tubular member 260 within the lumen 246 of the dilator 240. Optionally, the elongate tubular member 260 can omit the inclusion of fitting 271. In addition, the distal end 264 of the elongate tubular member 260 can optionally comprise a tapered portion. Optionally, the elongate tubular member can comprise a hydrophilic coating to potentially reduce the resistance of insertion and the likelihood of tissue damage.

The balloon 280 is disposed on the distal end 264 of the elongate tubular member 260 and is configured to move between a deflated configuration and an inflated configuration. The balloon 280 is illustrated in FIG. 2 in the inflated configuration. The body 282 of the balloon 280 and the portion of the exterior surface of the elongate tubular member 260 positioned within the balloon 280 define an inflation chamber 284. The balloon 280 is positioned on the distal end 264 of the elongate tubular member 260 such that opening 276 is in communication with the inflation chamber 284. With this structural arrangement, the balloon 280 can move between the deflated configuration and inflated configuration as fluid is moved into and out of the inflation chamber 284 via the opening 276, inflation lumen 270, and inflation port 266. In the deflated configuration, it is considered advantageous for the balloon 280 to be configured to adopt a folded configuration to allow for insertion of the elongate tubular member 260 and balloon 280 into the salivary duct opening and salivary duct and to allow for the dilator 260 to advance distally over the balloon 280. Optionally, the balloon 280 can omit adopting a folded configuration.

A user inflates the balloon 280 by introducing fluid (e.g., saline) into the inflation lumen 270 until the fluid passes through the opening 276 and into the inflation chamber 284. The resulting pressure placed on the inner surface of the balloon 280 by the fluid causes the balloon 280 to inflate and adopt the inflated configuration. To move the balloon 280 to the deflated configuration, vacuum pressure can be applied to the inflation lumen 270 to move fluid located within the inflation chamber 284, resulting in the balloon 280 collapsing and returning to a deflated configuration. Alternatively, the balloon 280 can be exposed (e.g., opened) to atmospheric pressures to move fluid located within the inflation chamber 284, resulting in the balloon 280 collapsing and returning to a deflated configuration. For example, advancing the sheath 220 and/or dilator 240 over the balloon 280 such that balloon 280, or a portion of balloon 280, is disposed in the lumen 226 of the sheath 220 and/or lumen 246 of the dilator 240, or withdrawing the balloon 280, or a portion of balloon 280, into the lumen 226 of the sheath 220 and/or lumen 246 of the dilator 240, provides a mechanism for removing fluid located within the inflation chamber 284 while the balloon 280 is in an inflated configuration, or partially inflated configuration, and exposed to atmospheric pressures and/or vacuum pressures.

The elongate tubular member 260 and balloon 280 can have any suitable length and inflated outside diameter. For example, the balloon 280 can have a length suitable to allow for the serial dilation of a portion, the entirety, or substantially the entirety, of the salivary duct tract. Alternatively, the balloon 280 can have a length suitable to allow for the dilation of the entire salivary duct tract, or substantially the entire salivary duct tract. It is considered advantageous to provide a balloon 280 that has an outside diameter greater than the outside diameter of the sheath 220 and/or dilator 240, to allow for the distal end of the sheath 240 and/or dilator 240 to pass through a dilated salivary duct opening and the portion of the salivary duct that has been dilated.

A marker 278 is disposed between the proximal end 262 and distal end 264 of the elongate tubular member 260. The marker 278 can be embedded within, or disposed on the exterior and/or interior surface of, the elongate tubular member 260. It is considered advantageous to position the marker 278 along the length of the elongate tubular member 260 at a location that is adjacent to the proximal end 242 of the dilator 240 when the distal end 244 of the dilator 240 is adjacent the proximal end of the balloon 280. For example, the marker 278 can be disposed a distance from the distal end 264 of the elongate tubular member 260 equal to, or substantially equal to, about the sum of the length of the balloon 280 and the length of the dilator 240. The positioning of the marker 278 in this manner allows a user to be informed as to the position of the distal end 244 of the dilator 240 in relation to the balloon 280. Alternative to the inclusion of the single marker 278, multiple markers can be included along the length of the elongate tubular member 260 to provide a user with an indication as to the distance the distal end 244 of the dilator 240 has traveled with respect to the balloon 280 and/or to provide a user with an indication as to the length of the elongate tubular member 260 disposed within the salivary duct. For example, markers can be provided along a portion of the length, or the entire length, of the elongate tubular member 260. Optionally, the inclusion of marker 278 can be omitted from the elongate tubular member 260.

Additional structure can be attached to the balloon catheter configurations described herein to facilitate the inflation and deflation of the balloon 280. For example, a syringe or other suitable structure can be attached to the inflation port 266 using any suitable connection, such as a luer lock connection. The fluid used to inflate the balloon 280 can be stored within the syringe and/or inflation lumen 270, and can be introduced into and removed from the inflation chamber 284 by operating the syringe using conventional practices.

The step 104 of advancing the distal end 204 of the balloon catheter 200 into the salivary duct such that a portion of the balloon 280 is disposed within the salivary duct can be accomplished by direct visualization. For example, after a user has inserted the distal end 204 of the balloon catheter 200 into the salivary duct, the user can apply a distal force on the balloon catheter 200 advancing the elongate tubular member 260 and/or balloon 280 through the salivary duct opening and into the salivary duct. Once the user has determined that a suitable length of the elongate tubular member 260 and/or balloon 280 has been advanced into the salivary duct, the user can stop applying the distal force to the balloon catheter 200. For example, the balloon 280 can optionally comprise one or more markers disposed along the length of the inner shaft 283 disposed within the length of the balloon 280. The markers can be disposed at various locations, such as at either end of the balloon, at the midpoint of the length of the balloon, and/or at any measured distance.

The step 106 of passing a fluid through the inflation lumen 270 and into the balloon 280 to move the balloon 280 from the deflated configuration to the inflated configuration and to dilate the salivary duct opening and the portion of the salivary duct contacting the balloon 280 can be accomplished by introducing a fluid into the opening 267 of the inflation port 266 and into the inflation chamber 284 of the balloon 280. By moving the balloon 280 from a deflated configuration to an inflated configuration, radial dilation of the salivary duct opening and/or salivary duct, or portions thereof, can be accomplished to allow for insertion of the sheath 220 and dilator 240. Examples of pressures considered suitable to inflate the balloon 280 and dilate the salivary duct opening and the portion of the salivary duct in contact with the balloon 280 include, but are not limited to, pressures in the range from about 2 ATM to about 16 ATM. In an example, the balloon 280 can have an outside diameter in the inflated configuration, which is greater than the outside diameter of the sheath 220, allowing for insertion of the sheath 220 and dilator 240 past the salivary duct opening and into the salivary duct. By over dilating the salivary duct opening and/or salivary duct, the pressures typically felt by a patient during insertion of the sheath 220 and dilator 240 can be decreased. While a balloon 280 having an outside diameter greater than the outside diameter of the sheath 220 has been described, other balloon sizes are considered suitable, and skilled artisans will be able to select an appropriate outside diameter for a balloon based on various considerations, such as the diameter of the salivary duct. Examples of outside diameters considered suitable for the balloon in the inflated configuration include outside diameters that are greater than, equal to, or less than the outside diameter of the sheath 220. Examples of fluids considered suitable to pass through the inflation lumen 270 into the balloon 280 include saline, water, contrast, or a mixture of one or more of saline, water, and/or contrast. While a particular fluid has been described as being passed into the balloon 280, other fluids are considered suitable, and a skilled artisan will be able to select an appropriate fluid according to a particular embodiment based on various considerations, such as the type of procedure being completed.

Alternative to dilating the salivary duct opening and the salivary duct, a user can dilate each of the salivary duct opening and the salivary duct separately. For example, an alternative step can comprise passing fluid through the inflation lumen 270 and into the balloon 280 to move the balloon 280 from the deflated configuration to the inflated configuration and to dilate the salivary duct opening. In another example, an alternative step can comprise passing fluid through the inflation lumen 270 and into the balloon 280 to move the balloon 280 from the deflated configuration to the inflated configuration to dilate a portion, or the entirety, of the salivary duct.

The step 108 of removing a portion, or the entirety, of the fluid from the balloon 280 can be accomplished by removing fluid passed into the inflation chamber 284. For example, a syringe in communication with the opening 267 of the inflation port 266 can be used to provide vacuum pressure to remove a portion, or the entirety, of the fluid from the inflation chamber 284. The amount of fluid removed from the inflation chamber 284 can vary depending on the procedure. For example, as described below, the amount of fluid removed can depend on the length of the dilator 240 passed over the balloon 280. In addition, the amount of fluid removed can depend on the length of the balloon 280. Alternatively, the inflation chamber 284 of the balloon 280 can be opened to atmospheric pressure and allowed to return to a deflated configuration as the sheath 220 and dilator 240 are advanced distally over the balloon 280, as described below.

The step 110 of advancing the sheath 220 and the dilator 240 over the elongate tubular member 260 and balloon 280 such that the distal end 224 of the sheath 220 and the distal end 244 of the dilator 240 are disposed within said salivary duct can be accomplished by a user applying a distal force on the fitting 248 of the dilator 240, or other portions of thereof, and maintaining the position of the elongate tubular member 260 to advance the sheath 220 and dilator 240 over a portion, or the entirety, of the elongate tubular member 260 and/or balloon 280. This step can be accomplished in a variety of alternative manners. In one alternative, this step can be accomplished in combination with the step of removing a portion, or the entirety, of the fluid from the balloon 280. This advantageously allows the sheath 220 and dilator 240 to be introduced into the salivary duct while it is in its dilated configuration. Alternatively, the balloon 280 can be opened to atmospheric pressure and the sheath 220 and dilator 240 can be advanced over a portion, or the entirety, of the elongate tubular member 260 and/or balloon 280. In this alternative, the fluid within the inflation chamber 284 of the balloon 280 is pushed out of the inflation chamber 284 as the dilator 240 and sheath 220 are advanced over the balloon 280. In another alternative, the sheath 220 and dilator 240 can be advanced over the elongate tubular member 260 and balloon 280 subsequent to the balloon 280 being deflated and returning to its deflated configuration. In another alternative, the balloon 280 and elongate tubular member 260 can be withdrawn from the salivary duct and salivary duct opening and then the sheath 220 and dilator 240 can be advanced into the salivary duct through the salivary duct opening independent of the elongate tubular member 260.

Alternatively, the step 110 of advancing the sheath 220 and the dilator 240 over the elongate tubular member 260 and balloon 280 such that the distal end 224 of the sheath 220 and the distal end 244 of the dilator 240 are disposed within a salivary duct can be accomplished in two steps. A step comprising advancing the dilator 240 over the elongate tubular member 260 and balloon 280 such that the distal end 244 of the dilator 240 is disposed within the salivary duct and a separate step comprising advancing the sheath 220 over the elongate tubular member 260 and balloon 280 such that the distal end 224 of the sheath 220 is disposed within the salivary duct.

In another alternative, the dilator 240 can be omitted from the balloon catheter 200 and the step of advancing the sheath 220 and the dilator 240 over the elongate tubular member 260 and balloon 280 such that the distal end 224 of the sheath 220 and the distal end 244 of the dilator 240 are disposed within said salivary duct can alternatively comprise advancing the sheath 220 over the elongate tubular member 260 and balloon 280 such that the distal end 224 of the sheath 220 is disposed within said salivary duct. This alternative step can be accomplished by a user applying a distal force on the proximal end 222 of the sheath 220, or other portions of thereof, and maintaining the position of the elongate tubular member 260 to advance the sheath 220 over a portion, or the entirety, of the elongate tubular member 260 and/or balloon 280. This step can be accomplished in a variety of alternative manners. In one alternative, this step can be accomplished in combination with the step of removing a portion, or the entirety, of the fluid from the balloon 280. This advantageously allows the sheath 220 to be introduced into the salivary duct while it is in its dilated configuration. Alternatively, the balloon 280 can be opened to atmospheric pressure and the sheath 220 can be advanced over a portion, or the entirety, of the elongate tubular member 260 and/or balloon 280. In this alternative, the fluid within the inflation chamber 284 of the balloon 280 is pushed out of the inflation chamber 284 as the sheath 220 is advanced over the balloon 280. In another alternative, the sheath 220 can be advanced over the elongate tubular member 260 and balloon 280 subsequent to the balloon 280 being deflated and returning to its deflated configuration. In another alternative, the balloon 280 and elongate tubular member 260 can be withdrawn from the salivary duct and salivary duct opening and then the sheath 220 can be advanced into the salivary duct through the salivary duct opening independent of the elongate tubular member 260.

In a further alternative, a step comprising withdrawing the balloon 280 and elongate tubular member 260 from the salivary duct and salivary duct opening can be completed and an optional step comprising advancing the dilator 240 into the salivary duct through the salivary duct opening towards a point of treatment independent of the elongate tubular member 260 can be accomplished. The dilator 240 can comprise a length suitable to be navigated through the entirety, or a portion, of the salivary duct. For example, it is considered advantageous to provide a dilator 240 with a length and flexibility configured to allow the dilator 240 to be advanced through the tortuosity of the salivary duct. Subsequent to advancing the dilator 240 towards a point of treatment, the sheath 220 can be advanced over the dilator 240 towards a point a point of treatment. This can be accomplished by holding the dilator 240 in place and advancing the sheath 220 proximally over the previously placed dilator 240. It is considered advantageous to advance each of the dilator 240 and sheath 220 separately to reduce the stiffness of the device traversing a portion of the length of the salivary duct.

The step 112 of withdrawing the dilator 240 and the elongate tubular member 260 from the salivary duct can be accomplished by applying a proximal force on the fitting 248 of the dilator 240 and sliding the dilator 240 proximally through the lumen 226 of the sheath 220. When the dilator 240 and the elongate tubular member 260 have been removed, the sheath 220 is left disposed within the salivary duct opening and the salivary duct, advantageously allowing for one or more devices to be inserted through the lumen 226 of the sheath 220 reducing the likelihood of trauma that may be caused to the salivary duct opening and salivary duct when a sheath 220 is not used. Alternatively, if the dilator has been omitted from the balloon catheter 200, step 112 can comprise withdrawing the elongate tubular member 260 from the salivary duct.

Alternatively, the step 112 of withdrawing the dilator 240 and the elongate tubular member 260 from said salivary duct can be accomplished in two separate steps. A step comprising withdrawing the elongate tubular member 260 from the salivary duct and the salivary duct opening by sliding the elongate tubular member 260 proximally through the lumen 246 of the dilator 240 and another step comprising withdrawing the dilator 240 from the salivary duct and salivary duct opening by sliding it proximally through the lumen 226 of the sheath 220.

An optional step comprises advancing one or more devices through the lumen 226 of the sheath 220 to provide treatment within the salivary duct and/or to the salivary glands. Example devices considered suitable for treatment of the salivary ducts and/or salivary glands include, but are not limited to, probes, scopes, cutting tools, elongate tubular members, endoscopes, stents, suction devices, graspers, forceps, lithotripters, balloons, drills, lasers, baskets, and any other device considered suitable for a particular application.

Another optional step comprises providing treatment within the salivary duct and/or to a salivary gland. Treatment can include, but is not limited to, removing a salivary stone, dilating a stricture within the salivary duct, delivering a therapeutic agent, and/or irrigating a salivary duct and/or irrigating salivary gland. In an example, an optional step comprises advancing a basket towards a point of treatment (e.g., a salivary stone disposed within the salivary duct). Another optional step comprises securing the salivary stone within the basket. Another optional step comprises withdrawing the basket and salivary stone from the lumen 226 of the sheath 220. In another example, an optional step comprises advancing a balloon catheter 200 towards a point of treatment (e.g., a stricture within the salivary duct). Another optional step comprises advancing the balloon catheter 200 proximal to, within, or distal to the stricture. Another optional step comprises passing a fluid into the balloon 280 to move the balloon 280 from a deflated configuration to an inflated configuration to dilate the stricture within the salivary duct. Another optional step comprises stopping the passing of fluid into the balloon 280. Another optional step comprises removing a portion, or the entirety, of the fluid from the balloon 280. Another step comprises withdrawing the balloon catheter 200 from the lumen 226 of the sheath 220. In another example, an optional step comprises advancing one or more of a lithotripter, drill, laser, grasper, retrieval device, and/or forceps to fragment and/or remove one or more salivary stones disposed within the salivary duct. In another example, an optional step comprises advancing one or more of a stent, suction, and/or drain to allow for a treatment to be completed.

Another optional step comprises withdrawing the sheath 220 from the salivary duct and salivary duct opening. This step can be accomplished by applying a proximal force on the proximal end 222 of the sheath 220, or other portion thereof, and removing the sheath 220 from the salivary duct and salivary duct opening.

While various catheter configurations, steps, alternative steps, and optional steps have been described above with respect to providing access to a salivary duct, these catheter configurations, steps, alternative steps, and optional steps can be included in, accomplished concurrently with, and/or accomplished in the alternative to, the methodologies, catheter configurations, steps, alternative steps, and/or optional steps described below with respect to the exemplary method of providing access 300 and the exemplary method of treatment 900.

Figure 3:
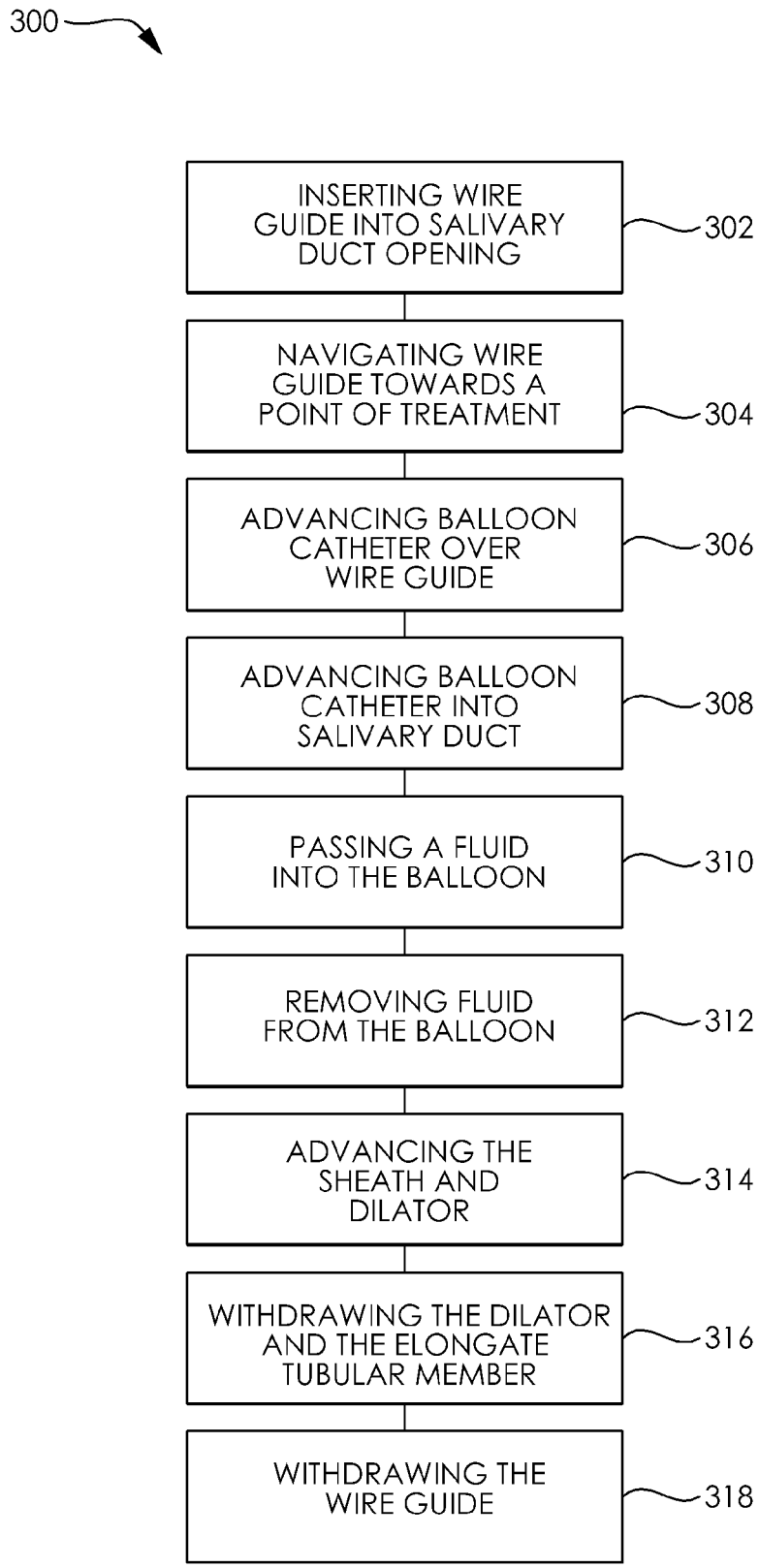
FIG. 3 is a flowchart representation of another exemplary method of treatment.

FIG. 3 is a flowchart representation of another exemplary method 300 of providing access to a salivary duct having a salivary duct opening using a balloon. The method is similar to that described above with respect to method 100, except as described below. An initial step 302 comprises inserting a wire guide having a proximal end and a distal end into a salivary duct opening such that the distal end of the wire guide is disposed within the salivary duct. Another step 304 comprises navigating the distal end of the wire guide towards a point of treatment within the salivary duct. Another step 306 comprises advancing a balloon catheter having a proximal end and a distal end over the previously placed wire guide. The balloon catheter comprises a sheath, a dilator, an elongate tubular member, and a balloon. The sheath has a proximal end, a distal end, and defines a lumen extending between openings located at the proximal end and distal end of the sheath. The dilator is slidably disposed within the lumen of the sheath and has a proximal end, a distal end, and defines a lumen extending between openings located at the proximal end and distal end of the dilator. The elongate tubular member is slidably disposed within the lumen of the dilator and has a proximal end, a distal end, and defines an inflation port, a lumen, an inflation lumen, and an inflation lumen opening. The lumen of the elongate tubular member extends between openings located at the proximal end and distal end of the elongate tubular member and the inflation lumen extends between an opening in the inflation port and the inflation lumen opening disposed between the proximal end and the distal end of the elongate tubular member. The balloon is disposed on the distal end of the elongate tubular member, is in communication with the inflation lumen opening, and is moveable between a deflated configuration and an inflated configuration. Another step 308 comprises advancing the distal end of the balloon catheter over the previously placed wire guide such that the distal end of the catheter is disposed in said salivary duct. Another step 310 comprises passing a fluid through the inflation lumen and into the balloon to move the balloon from the deflated configuration to the inflated configuration and to dilate the salivary duct opening and the portion of the salivary duct contacting the balloon. Another step 312 comprises removing a portion, or the entirety, of the fluid from the balloon. Another step 314 comprises advancing the sheath and the dilator over the elongate tubular member and balloon such that the distal end of the sheath and the distal end of the dilator are disposed within said salivary duct. Another step 316 comprises withdrawing the dilator and the elongate tubular member from the salivary duct. Another step 318 comprises withdrawing the wire guide from the salivary duct.

The step 302 of inserting the distal end of the wire guide into a salivary duct opening such that the distal end of the wire guide is disposed within the salivary duct can be accomplished using direct visualization and with a wire guide having any suitable length and formed of any suitable material. Conventional wire guides are considered suitable.

The step 304 of navigating the distal end of the wire guide towards a point of treatment can be accomplished using direct visualization and/or with the aid of a scope. For example, an optional step comprises inserting a scope into a salivary duct opening such that the distal end of the scope is disposed within the salivary duct. Another optional step comprises advancing the scope over the previously placed wire guide. This step can be accomplished by placing the proximal end of the wire guide into a lumen defined by the scope and advancing the scope distally over the wire guide. Another optional step comprises advancing the scope towards a point of treatment within the salivary duct.

Figure 4:
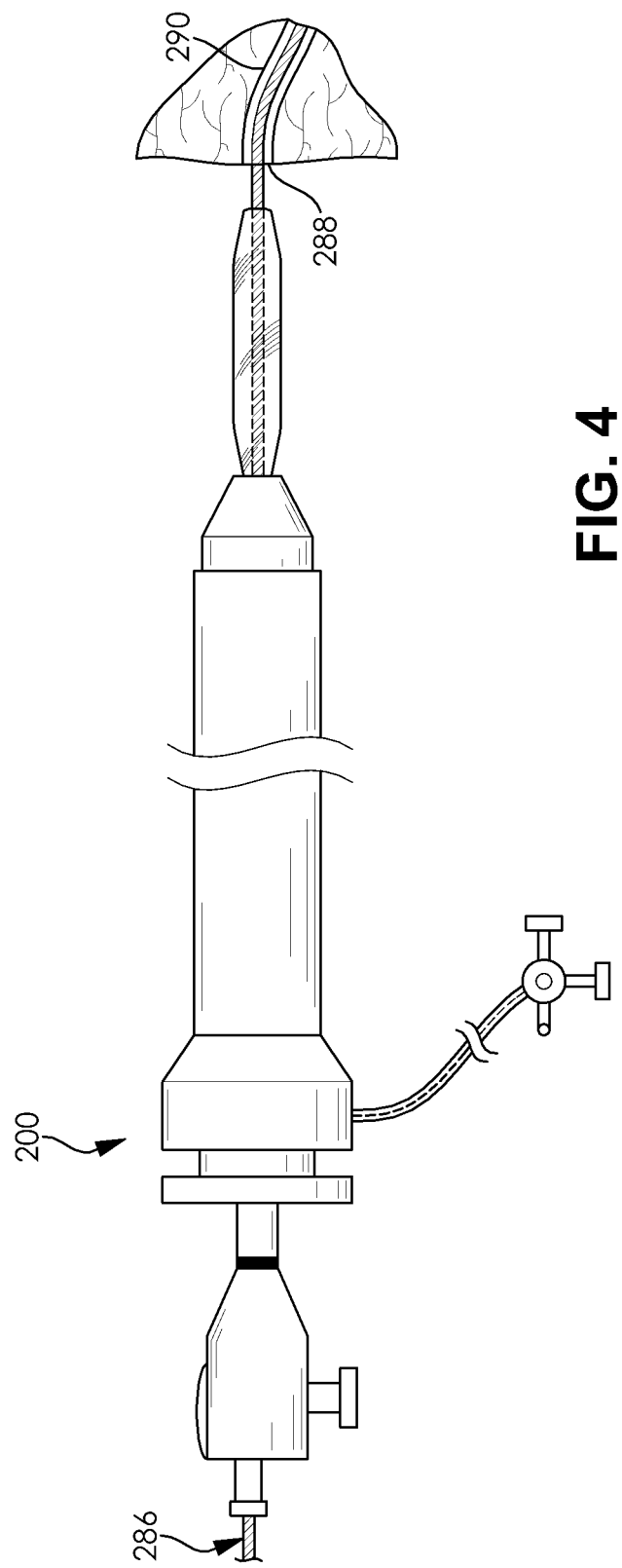
FIG. 4 is a side view of the exemplary balloon catheter illustrated in FIG. 2 advanced over a previously placed wire guide.

The step 306 of advancing the balloon catheter 200 over the previously placed wire guide can be accomplished by inserting the proximal end of the wire guide through the lumen 268 defined by the elongate tubular member 260 and advancing the catheter 200 distally over the previously placed wire guide. FIG. 4 illustrates a catheter 200 disposed over a previously placed wire guide 286. The wire guide 286 has been inserted past the salivary duct opening 288 and navigated towards a point of treatment within the salivary duct 290.

The step 308 of advancing the distal end 204 of the balloon catheter 200 over the previously placed wire guide 286 such that the distal end 204 of the balloon catheter 200 is disposed in said salivary duct 290 can be accomplished by applying a distal force on a portion of the balloon catheter 200 (e.g., the fitting 271 of the elongate tubular member 260, the fitting 248 of the dilator 240) to advance the catheter 200 over the previously placed wire guide 286 past the salivary duct opening 288 and into the salivary duct 290.

The step 310 of passing a fluid through the inflation lumen 270 and into the balloon 280 to move the balloon 280 from the deflated configuration to the inflated configuration and to dilate the salivary duct opening 288 and the portion of the salivary duct 290 contacting the balloon 280 can be accomplished by introducing a fluid into the opening 267 of the inflation port 266 and through the inflation lumen 270 into the inflation chamber 284. FIG. 5 illustrates a balloon 280 in an inflated configuration dilating both the salivary duct opening 288 and a portion of the salivary duct 290. The marker 278 located adjacent to the fitting 248 of the dilator 240 indicates to a user that the distal end 244 of the dilator 240 is adjacent to the proximal end of the balloon 280. Alternative to dilating a portion of the salivary duct 290, the length of the elongate tubular member 260 and balloon 280 can vary to allow for the dilation of the entirety of the tract of the salivary duct 290, or substantially the entirety of the tract of the salivary duct 290.

The step 312 of removing a portion, or the entirety, of the fluid from the balloon 280 can be accomplished by applying vacuum pressure to the inflation lumen 270 to remove fluid located within the inflation chamber 284, resulting in the balloon 280 collapsing and returning to a deflated configuration. Alternatively, the balloon 280 can be exposed (e.g., opened) to atmospheric pressures to move fluid located within the inflation chamber 284, resulting in the balloon 280 collapsing and returning to a deflated configuration. For example, advancing the sheath 220 and/or dilator 240 over the balloon 280 such that balloon 280, or a portion of balloon 280, is disposed in the lumen 226 of the sheath 220 and/or lumen 246 of the dilator 240, or withdrawing the balloon 280, or a portion of balloon 280, into the lumen 226 of the sheath 220 and/or lumen 246 of the dilator 240, provides a mechanism for removing fluid located within the inflation chamber 284.

The step 314 of advancing the sheath 220 and the dilator 240 over the elongate tubular member 260 and balloon 280 such that the distal end 224 of the sheath 220 and the distal end 244 of the dilator 240 are disposed within said salivary duct 290 can be accomplished by a user applying a distal force on the fitting 248 of the dilator 240, or other portions thereof, and maintaining the position of the elongate tubular member 260. The distal force on the dilator 240 advances the sheath 220 and dilator 240 in a distal direction over the elongate tubular member 260 and balloon 280. This step can be accomplished in a variety of alternative manners, as described above. FIG. 6 illustrates the sheath 220 and dilator 240 advanced distally over the elongate tubular member 260 and balloon 280 in the direction of arrows 292 such that the distal end 224 of the sheath 220 and the distal end 244 of the dilator 240 are disposed within the salivary duct 290 passed the salivary duct opening 288.

In an alternative, the dilator 240 can be omitted from the balloon catheter 200 and the step of advancing the sheath 220 and the dilator 240 over the elongate tubular member 260 and balloon 280 such that the distal end 224 of the sheath 220 and the distal end 244 of the dilator 240 are disposed within said salivary duct can alternatively comprise advancing the sheath 220 over the elongate tubular member 260 and balloon 280 such that the distal end 224 of the sheath 220 is disposed within said salivary duct. This alternative step can be accomplished by a user applying a distal force on the proximal end 222 of the sheath 220, or other portions of thereof, and maintaining the position of the elongate tubular member 260 to advance the sheath 220 over a portion, or the entirety, of the elongate tubular member 260 and/or balloon 280. This step can be accomplished in a variety of alternative manners. In one alternative, this step can be accomplished in combination with the step of removing a portion, or the entirety, of the fluid from the balloon 280. This advantageously allows the sheath 220 to be introduced into the salivary duct while it is in its dilated configuration. Alternatively, the balloon 280 can be opened to atmospheric pressure and the sheath 220 can be advanced over a portion, or the entirety, of the elongate tubular member 260 and/or balloon 280. In this alternative, the fluid within the inflation chamber 284 of the balloon 280 is pushed out of the inflation chamber 284 as the sheath 220 is advanced over the balloon 280. In another alternative, the sheath 220 can be advanced over the elongate tubular member 260 and balloon 280 subsequent to the balloon 280 being deflated and returning to its deflated configuration. In another alternative, the balloon 280 and elongate tubular member 260 can be withdrawn from the salivary duct and salivary duct opening and then the sheath 220 can be advanced into the salivary duct through the salivary duct opening independent of the elongate tubular member 260.

The step 316 of withdrawing the dilator 240 and the elongate tubular member 260 from the salivary duct can be accomplished by applying a proximal force on the fitting 248 of the dilator 240 and sliding the dilator 240 proximally through the lumen 226 of the sheath 220. When the dilator 240 and the elongate tubular member 260 have been removed, the sheath 220 is left disposed within the salivary duct opening and the salivary duct, advantageously allowing for one or more devices to be inserted through the lumen 226 of the sheath 220 reducing the likelihood of trauma that may be caused to the salivary duct opening and salivary duct when a sheath 220 is not used. Alternatively, if the dilator has been omitted from the balloon catheter 200, step 316 can comprise withdrawing the elongate tubular member 260 from the salivary duct.

Alternatively, the step 316 of withdrawing the dilator 240 and the elongate tubular member 260 from said salivary duct can be accomplished in two separate steps. A step comprising withdrawing the elongate tubular member 260 from the salivary duct and the salivary duct opening by sliding the elongate tubular member 260 proximally through the lumen 246 of the dilator 240 and another step comprising withdrawing the dilator 240 from the salivary duct and salivary duct opening by sliding it proximally through the lumen 226 of the sheath 220.

Figure 7:
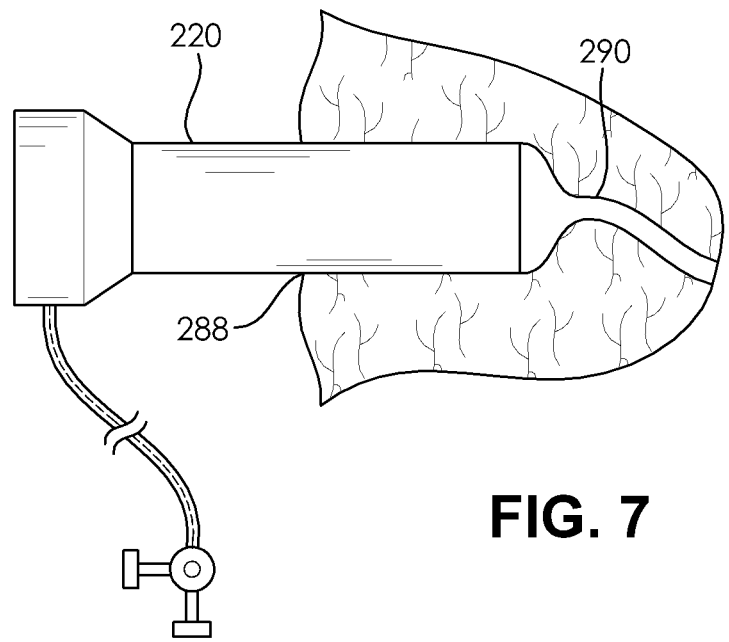
FIG. 7 is a side view of a portion of a sheath disposed in a salivary duct.

The step 318 of withdrawing the distal end of the wire guide 286 from the salivary duct 290 through the salivary duct opening 288 can be accomplished by applying a proximal force on a portion of the wire guide 286 (e.g., the proximal end of the wire guide) until the wire guide 286 is completely removed from the salivary duct 290. Optionally, the step 316 of withdrawing the distal end of the wire guide 286 from the salivary duct 290 through the salivary duct opening 288 can be accomplished in combination with withdrawing the dilator 240 and elongate tubular member 260. FIG. 7 illustrates the completion of the steps of withdrawing the dilator 240, the elongate tubular member 260, and the wire guide 286 from the salivary duct 290. Therefore, FIG. 7 illustrates a sheath 220 disposed within a portion of the salivary duct 290. As discussed above, leaving a sheath 220 disposed within the salivary duct opening 288 and a portion of the salivary duct 290 is considered advantageous to allow for one or more devices to traverse the lumen 226 of the sheath 220 to provide treatment to the salivary duct 290 or a salivary gland.

Figure 8:
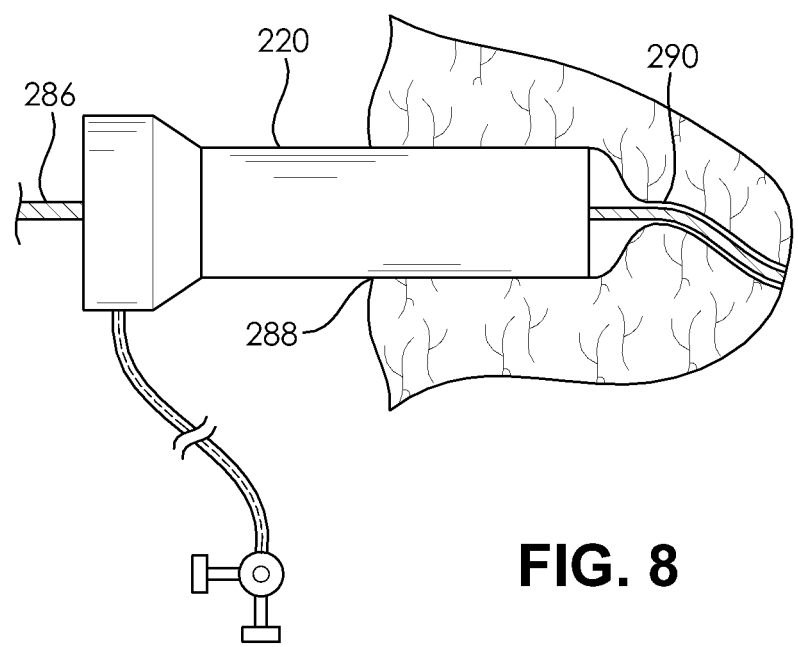
FIG. 8 is a side view of a portion of a sheath and wire guide disposed in a salivary duct.

Alternative to withdrawing the distal end of the wire guide 286 from the salivary duct 290 through the salivary duct opening 288, the wire guide 286 can remain in the salivary duct 290, as illustrated in FIG. 8. Leaving the wire guide 286 disposed within the salivary duct 290 is considered advantageous to allow for one or more devices to be advanced over the previously placed wire guide 286 towards a point of treatment, potentially reducing the occurrence of perforation of the wall of the salivary duct 290 by insertion and advancement of the one or more devices.

For example, an optional step comprises advancing one or more devices through the lumen 226 of the sheath 220 and/or over the previously placed wire guide 286 to provide treatment within the salivary duct 290 and/or to a salivary gland. Example devices considered suitable for treatment of the salivary ducts and/or salivary glands, include, but are not limited to, probes, scopes, cutting tools, elongate tubular members, endoscopes, stents, suction devices, graspers, forceps, lithotripters, balloons, drills, lasers, baskets, and any other device considered suitable for a particular application. Treatment can include, but is not limited to, delivering a therapeutic agent, removing a salivary stone and/or dilating a stricture within the salivary duct.

While various catheter configurations, steps, alternative steps, and optional steps have been described above with respect to providing access to a salivary duct, these catheter configurations, steps, alternative steps, and optional steps can be included in, accomplished concurrently with, and/or accomplished in the alternative to, the methodologies, catheter configurations, steps, alternative steps, and/or optional steps described above with respect to exemplary method of providing access 100 and below with respect to exemplary method of treatment 900.

Figure 9:
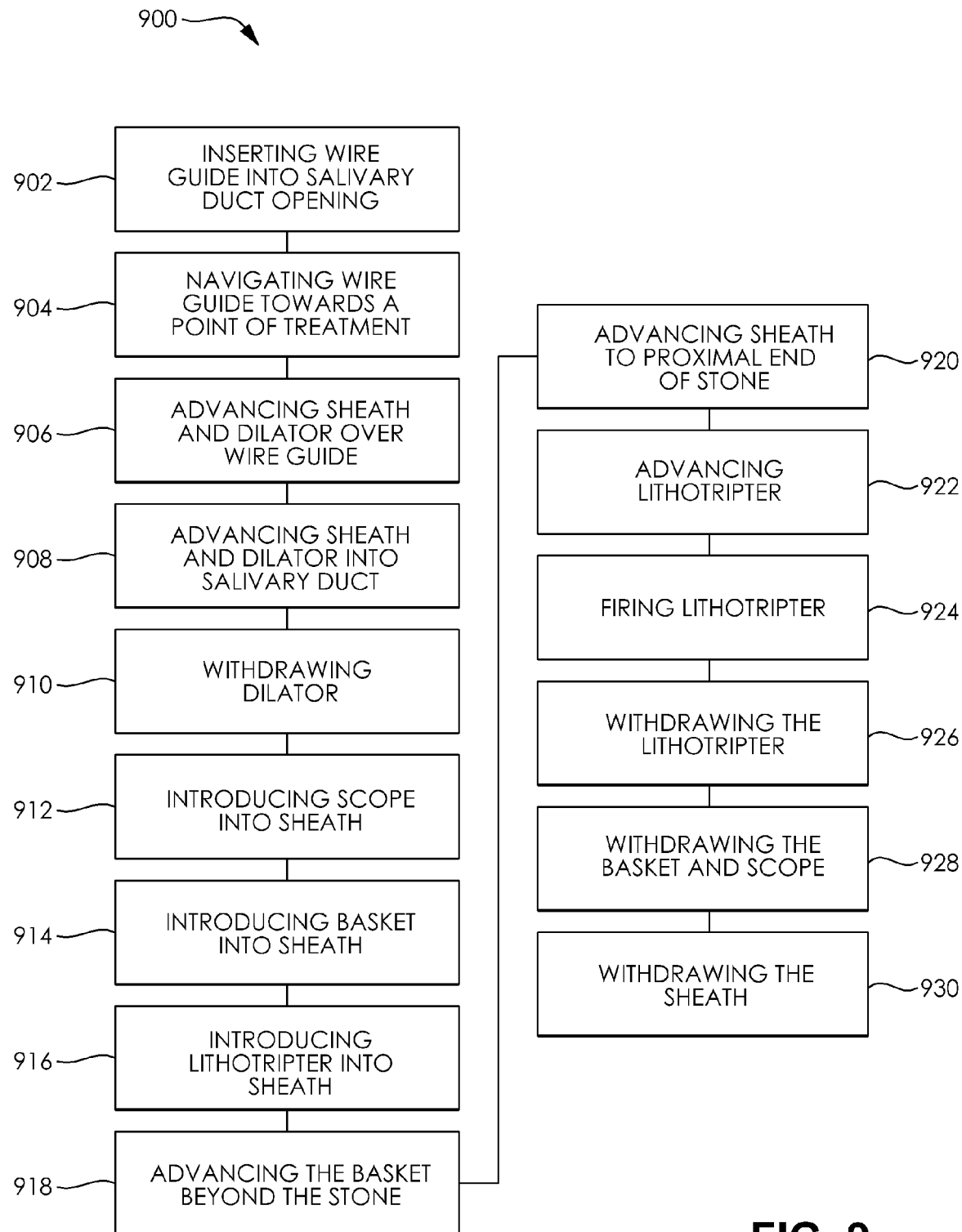
FIG. 9 is another exemplary method of treatment.

FIG. 9 is a flowchart representation of another exemplary method 900 of providing treatment to a salivary duct having a salivary duct opening using a sheath and dilator. While method 900 is exemplified by methods of providing access to a salivary duct and removing one or more salivary stones contained within the salivary duct, the method 900, and/or one or more of the steps described in association with method 900, can be used to treat other conditions within the salivary duct and/or another bodily passage.

The method 900 is similar to that described above with respect to method 300, except as described below. An initial step 902 comprises inserting a wire guide having a proximal end and a distal end into a salivary duct opening such that the distal end of the wire guide is disposed within the salivary duct. Another step 904 comprises navigating the distal end of the wire guide towards a point of treatment within the salivary duct. Another step 906 comprises advancing a sheath and dilator, each having a proximal end and a distal end, over the previously placed wire guide. The sheath has a proximal end, a distal end, a valve disposed on the proximal end of the sheath, a side arm, and defines a lumen extending between the proximal end and an opening located at the distal end of the sheath. The dilator is slidably disposed within the lumen of the sheath and has a proximal end, a distal end, and defines a lumen extending between openings located at the proximal end and distal end of the dilator. Another step 908 comprises advancing the distal end of the sheath and the distal end of the dilator over the previously placed wire guide such that the distal end of the sheath and the distal end of the dilator are disposed in the salivary duct. Another step 910 comprises withdrawing the dilator. Another step 912 comprises introducing a scope having a proximal end and a distal end into the proximal end of the sheath such that the distal end of the scope is disposed within the salivary duct. Another step 914 comprises introducing a basket having a proximal end and a distal end into the proximal end of the sheath such that the distal end of the basket is disposed within the salivary duct. Another step 916 comprises introducing a lithotripter having a proximal end and a distal end into the proximal end of the sheath such that the distal end of the lithotripter is disposed within the salivary duct. Another step 918 comprises advancing the distal end of the basket beyond the salivary stone. Another step 920 comprises advancing the distal end of the sheath to the proximal end of the salivary stone. Another step 922 comprises advancing the lithotripter to the proximal end of the salivary stone. Another step 924 comprises firing the lithotripter. Another step 926 comprises withdrawing the lithotripter from the salivary duct. Another step 928 comprises withdrawing the basket and scope from the salivary duct. Another step 930 comprises withdrawing the sheath from the salivary duct and salivary duct opening.

Figure 10:
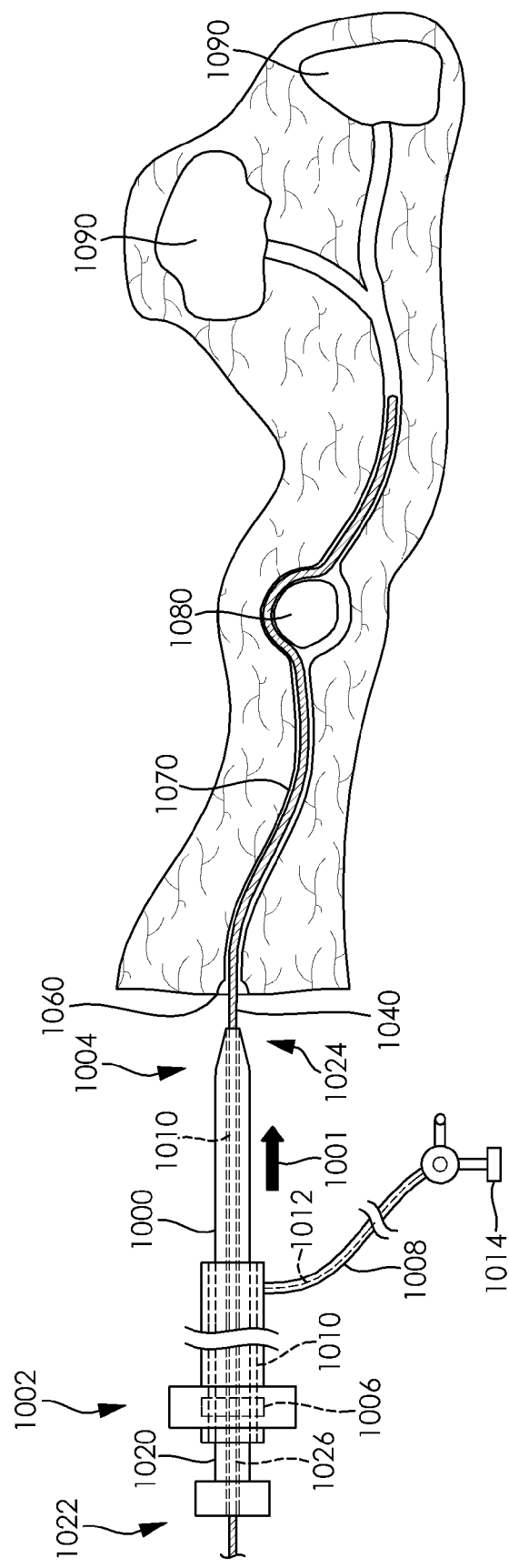
FIG. 10 is a side view of an exemplary sheath and dilator being advanced over a previously placed wire guide.
Figure 11:
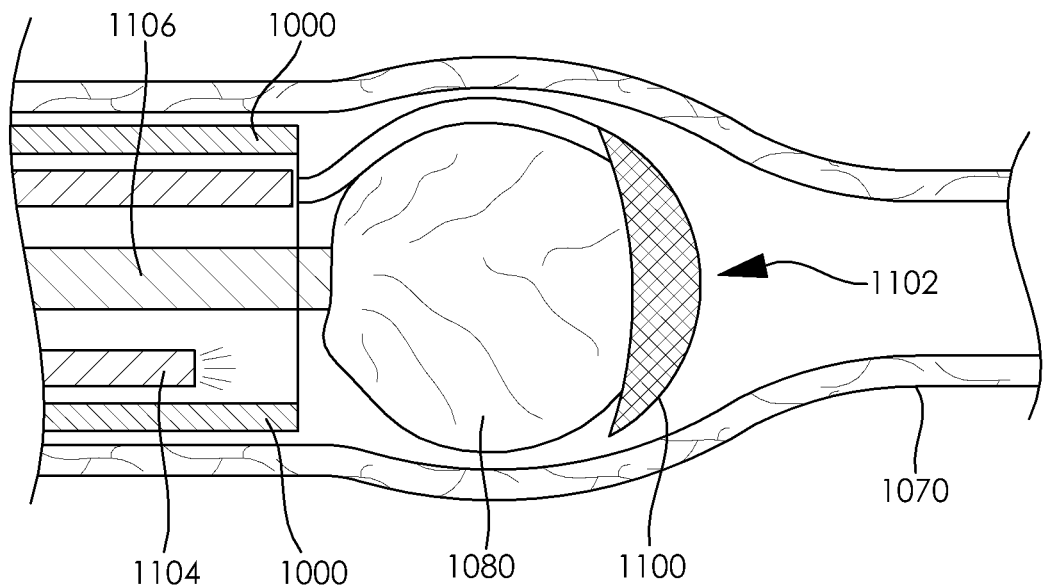
FIG. 11 is a side view of an exemplary basket, lithotripter, scope, and sheath disposed within a salivary duct.

FIGS. 10 and 11 illustrate an exemplary sheath 1000 and dilator 1020 being advanced over a previously placed wire guide 1040 in the direction of arrow 1001. The wire guide 1040 has been advanced past the papilla 1060, into the salivary duct 1070, and towards a point of treatment (e.g., salivary stone 1080). Salivary glands 1090 have also been illustrated.

The sheath 1000 has a proximal end 1002, a distal end 1004, a valve 1006 disposed on the proximal end 1002 of the sheath 1000, and a side arm 1008. A lumen 1010 is defined extending between the proximal end 1002 and an opening located at the distal end 1004 of the sheath 1000. The valve 1006 can comprise any suitable sealing member (e.g., one-way valve, elastic valve) which prevents the flow of fluid through the proximal end 1002 of the sheath and/or creates a seal (e.g., adapts to the profiles of the devices inserted through the valve 1006) around one or more devices passing through the proximal end 1002 of the sheath 1000. It is considered advantageous for the sheath 1000 to comprise a valve 1006 on the proximal end 1002 of the sheath 1000 to maintain fluid introduced into the salivary duct 1070 (e.g., via side arm 1008, or other ancillary devices passed through the sheath) and to reduce the need for constant infusion of fluid during a procedure.

While sheath 1000 has been illustrated and described as including a valve 1006 disposed on the proximal end 1002 of the sheath 1000, valve 1006 can be omitted from inclusion with sheath 1000 such that sheath 1000 has a proximal end, a distal end, and a side arm. It is considered advantageous for sheath 1000 to omit the inclusion of valve 1006 to provide a mechanism for irrigating the point of treatment, or the area around the point of treatment, such that the field of view can be cleared of material (e.g., stone fragments) to allow a stone basket to remove stones, or stone fragments.

The side arm 1008 comprises a wall that defines a lumen 1012 and a valve 1014. The lumen 1012 is in fluid communication with the lumen 1010 of the sheath. The side arm 1008 advantageously allows for fluid to be introduced into the lumen 1010 of the sheath 1000 and into a salivary duct 1070, which allows for dilation of the salivary duct 1070. The sidearm 1008 allows for excess fluid to drain from the duct if it is injected through an ancillary device passed through the sheath lumen 1010. Alternatively, fluid may be injected into lumen 1010 and 1012 as needed through 1008. The side arm is configured to prevent fluid from leaking from the salivary duct 1070 and/or the sheath 1000 during the performance of a procedure. The distal end 1004 of the sheath 1000 can optionally comprise a tapered portion. In addition, the sheath 1000 can optionally comprise a hydrophilic coating to potentially reduce the resistance of insertion and the likelihood of tissue damage. Optionally, side arm 1008 can be omitted from sheath 1000.

Alternatively, when valve 1006 is omitted from sheath 1000, suction can be applied to lumen 1012 defined by the wall of side arm 1008 such that material can be removed from a point of treatment, or an area around a point of treatment. For example, if fluid is introduced in the lumen 1010 of sheath 1000 and into a salivary duct, or at another point of treatment, applying suction to lumen 1012 will draw fluid through lumen 1010 defined by sheath 1000 and through lumen 1012 defined by side arm 1008.

The dilator 1020 is slidably disposed within the lumen 1010 of the sheath 1000 and has a proximal end 1022 and a distal end 1024. The dilator 1020 defines a lumen 1026 extending between openings located at the proximal end 1022 and distal end 1024 of the dilator 1020. The dilator 1020 can be preloaded within the sheath 1000 or provided separately from sheath 1000 and subsequently loaded into the sheath 1000. The distal end 1024 of the dilator 1020 can optionally comprise a tapered portion that is configured to provide a transition-less, or substantially transition-less, progression between the dilator 1020 and the sheath 1000. To accomplish a transition-less, or substantially transition-less, configuration the sheath 1000 is tapered to a very thin wall at its distal end 1004 and the outside diameter of the distal end 1024 of the dilator 1020 is substantially equal, or equal to, the inside diameter of the sheath 1000 such that the transition between the dilator 1020 and sheath 1000 reduce, or eliminate, the existence of a ledge between the distal end 1004 of the sheath 1000 and the outside diameter of the dilator 1020. Optionally, the dilator can comprise a hydrophilic coating to potentially reduce the resistance of insertion and the likelihood of tissue damage.

The step 902 of inserting a wire guide having a proximal end and a distal end into a salivary duct opening such that the distal end of the wire guide is disposed within the salivary duct and the step 904 of navigating the distal end of the wire guide towards a point of treatment within the salivary duct are both optional and can be omitted to allow a sheath and/or dilator to be passed through a salivary duct opening and into a salivary duct.

The step 906 of advancing a sheath 1000 and dilator 1020 over the previously placed wire guide 1040 can be accomplished by inserting the proximal end of the wire guide 1040 through the lumen 1026 defined by the dilator 1020 and advancing the sheath 1000 and dilator 1020 distally over the previously placed wire guide 1040. Optional steps comprising advancing a dilator (e.g., balloon catheter) over the previously placed wire guide 1040 and dilating the opening of the salivary duct can be accomplished prior to advancement of the sheath and dilator over the previously placed wire guide.

The step 908 of advancing the distal end of the sheath 1000 and the distal end of the dilator 1020 over the previously placed wire guide 1040 such that the distal end of the sheath 1000 and the distal end of the dilator 1020 are disposed within the salivary duct can be accomplished by advancing the distal end 1004 of the sheath 1000 and the distal end 1024 of the dilator 1020 distally over the previously placed wire guide 1040 until the distal end 1004 of the sheath 1000 and the distal end 1024 of the dilator 1020 have been advanced past the papilla 1060.

The step 910 of withdrawing the dilator 1020 can be accomplished by pulling the dilator 1020 proximally through the lumen 1010 defined by the sheath 1000 until the dilator 1020 has been removed from the salivary duct, sheath 1000, and/or from the wire guide 1040.

The step 912 of introducing a scope (e.g., diagnostic scope, interventional scope) having a proximal end and a distal end into the proximal end of the sheath 1000 such that the distal end of the scope is disposed within the salivary duct, the step 914 of introducing a basket having a proximal end and a distal end into the proximal end of the sheath 1000 such that the distal end of the basket is disposed within the salivary duct, and the step 916 of introducing a lithotripter having a proximal end and a distal end into the proximal end of the sheath 1000 such that the distal end of the lithotripter is disposed within the salivary duct can each be accomplished by inserting the distal end of the scope, the distal end of the basket, and the distal end of the lithotripter into the lumen 1010 of the sheath 1000 and advancing the distal end of the scope, the distal end of the basket, and the distal end of the lithotripter distally until the distal end of the scope, the distal end of the basket, and the distal end of the lithotripter are disposed within the salivary duct. These steps can be accomplished separately, or in combination with one another. It is considered advantageous to initially introduce the distal end of the scope into the salivary duct, to allow for visualization of the salivary duct and/or treatment site prior to advancement of other devices. However, these steps can be performed in any suitable order.

Figure 12:
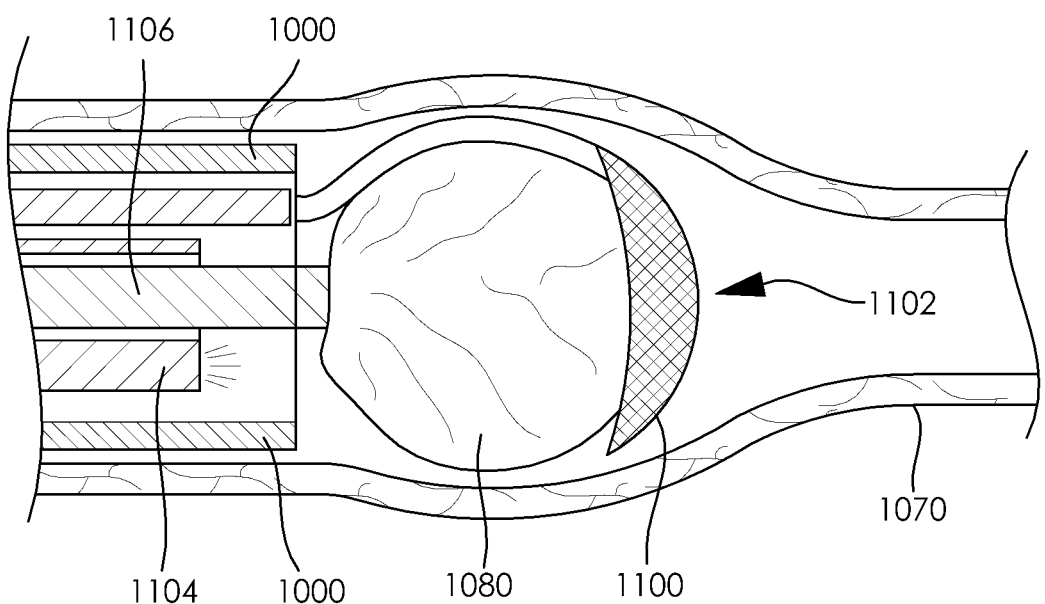
FIG. 12 is a side view of another exemplary basket, lithotripter, scope, and sheath disposed within a salivary duct.

A scope having a distal end introduced and passed through lumen 1010 of sheath 1000 such that it is disposed within a salivary duct can optionally include a working channel defined by the wall of the scope that extends from an opening defined on the proximal end of the scope to an opening defined on the distal end of the scope. The inclusion of a working channel of a scope is considered advantageous at least because it provides a passageway to introduce and pass a secondary device such that the distal end of the secondary device can be positioned at a point of treatment. This can be accomplished by introducing the secondary device distal end into the working channel, advancing the distal end distally through the working channel, and positioning the distal end at a point of treatment. FIG. 12 illustrates a lithotripter 1106 disposed through the working channel 1108 of a scope 1104. Skilled artisans will be able to select a suitable secondary device to pass through the working channel of a scope according to a particular embodiment based on various considerations, including the procedure intended to be performed. Example secondary devices considered suitable to pass through the working channel of a scope include, but are not limited to, a lithotripter, basket, or any other device considered suitable for a particular application.

Alternatively, step 914 of introducing a basket having a proximal end and a distal end into the proximal end of the sheath 1000 such that the distal end of the basket is disposed within the salivary duct and/or step 916 of introducing a lithotripter having a proximal end and a distal end into the proximal end of the sheath 1000 such that the distal end of the lithotripter is disposed within the salivary duct can each be accomplished by inserting the distal end of the basket and/or the distal end of the lithotripter into the working channel of a scope.

Subsequent to completing the step of introducing a scope having a proximal end and a distal end into the proximal end of the sheath 1000 such that the distal end of the scope is disposed within the salivary duct 1070, an optional step comprising withdrawing the distal end of the wire guide 1040 from the salivary duct 1070 can be completed. The step of withdrawing the distal end of the wire guide 1040 from the salivary duct 1070 through the salivary duct opening 1060 can be accomplished by applying a proximal force on a portion of the wire guide 1040 (e.g., the proximal end of the wire guide) until the wire guide 1040 is completely removed from the salivary duct 1070.

Optionally, a step comprising introducing fluid into the side arm 1008 can be completed prior to, or in combination, with the step of inserting a scope into the salivary duct 1070. This step advantageously provides for distending the wall of the salivary duct 1070 to allow for visualization of the salivary duct 1070 and/or a point of treatment. Another optional step comprises introducing fluid through the scope and into the salivary duct 1070 to distend the salivary duct 1070. The valve 1014 directs excess fluid to be directed through lumen 1012. Another optional step comprises applying vacuum pressure to the lumen 1012 defined by the wall of side arm 1008 while fluid is being introduced through a passageway defined by the wall of a scope (e.g., lumen defined by the wall of a scope).

The step 918 of advancing the basket beyond the salivary stone 1080 can be accomplished by visualizing the salivary stone through the scope and advancing the distal end of the basket distally until it has reached a position that is distal to the salivary stone. FIG. 11 illustrates the distal end 1102 of a basket 1100 positioned distal to a salivary stone 1080 located within a salivary duct 1070. Alternatively, the basket 1100 can be advanced distally to a point along the length of the salivary stone 1080, or proximal to the salivary stone 1080. An optional step comprises deploying the basket 1100 at a point distal to, along the length, or proximal to the salivary stone 1080. Another optional step comprises pulling the distal end 1102 of the basket 1100 proximally such that the basket contacts the salivary stone 1080. Optionally, the step 918 of advancing the basket beyond the salivary stone 1080 can be omitted.

The step 920 of advancing the sheath 1000 to the proximal end of the salivary stone 1080 can be accomplished by visualizing the salivary stone 1080 through the scope 1104 and advancing the distal end 1004 of the sheath 1000 distally until it is in contact with the proximal end of the salivary stone 1080, or at a location that is positioned near the proximal end of the salivary stone 1080. Alternatively, this step can comprise advancing the sheath 1000 to a position proximal to the salivary stone 1080. It is considered advantageous to advance the distal end of the sheath 1000 to at, or near, the proximal end of the salivary stone 1080 to allow for the removal of one or more salivary stone fragments and to decrease the potential for the distal end of the lithotripter 1106 to contact the wall of the salivary duct 1070 during performance of a procedure. Optionally, the step 920 of advancing the sheath 1000 to the proximal end of the salivary stone 1080 can be omitted.

The step 922 of advancing the lithotripter 1106 to the proximal end of the salivary stone 1080 can be accomplished by visualizing the salivary stone 1080 through the scope 1104 and advancing the distal end of the lithotripter 1106 distally until it contacts the proximal end of the salivary stone 1080, or is positioned near the proximal end of the salivary stone 1080. The lithotripter 1106 can comprise any suitable device for fragmenting a salivary stone 1080 located within a salivary duct 1070. Examples of lithotripters 1106 considered suitable include, but are not limited to, laser lithotripters and/or pneumatic lithotripters.

The step 924 of firing the lithotripter 1106 can be accomplished by a user activating the lithotripter 1106 (e.g., via switch, pedal, trigger). When the lithotripter 1106 is activated, the distal end of the lithotripter 1106 is utilized to fragment the salivary stone 1080 to allow for the salivary stone 1080, or fragments thereof, to be removed from the salivary duct 1070 through the sheath 1000. The steps of advancing the lithotripter 1106 to the proximal end of the salivary stone 1000 and firing the lithotripter 1106 can optionally be repeated as necessary to fragment the salivary stone 1080 to a desired size.

Alternatively, the step of advancing the basket beyond the salivary stone and/or the step of advancing the sheath 1000 to the proximal end of the salivary stone 1080 can be accomplished subsequent to the step of advancing the lithotripter 1106 to the proximal end of the salivary stone 1080. In a further alternative, the step of advancing the basket beyond the salivary stone and/or the step of advancing the sheath 1000 to the proximal end of the salivary stone 1080 can be accomplished subsequent to the step of firing the lithotripter 1106.

The step 926 of withdrawing the lithotripter 1106 can be accomplished by applying a proximal force on the lithotripter 1106 (e.g., the proximal end of the lithotripter 1106) until the lithotripter 1106 is removed from the salivary duct and/or the sheath 1000. Alternatively, when the scope defines a working channel, the step 926 of withdrawing the lithotripter can be accomplished by applying a proximal force on the lithotripter until the lithotripter is removed from the salivary duct and the working channel of a scope.

The step 928 of withdrawing the basket and scope can be accomplished by applying a proximal force on the basket and scope until the distal end of the basket and the distal end of the scope are removed from the salivary duct 1070 and/or sheath 1000. While the step of withdrawing the basket 1100 and scope 1104 has been described as removing both devices simultaneously, the basket 1100 and scope 1104 can be withdrawn from the salivary duct 1070 separately, or in combination with withdrawing the lithotripter 1106 from the salivary duct 1070. Optionally, a step comprising confirming that one or more salivary stones are contained within the basket 1100 prior to withdrawing the basket 1100 can be accomplished prior to withdrawing the basket 1100 from the salivary duct 1070 and/or sheath 1000. Another optional step comprises re-inserting the scope 1104 and/or basket 1100 into the salivary duct 1070 can be accomplished. Another optional step can comprise capturing one or more salivary stone fragments within the basket 1100 and withdrawing the basket from the salivary duct and/or sheath 1000.

The step 930 of withdrawing the sheath 1000 from the salivary duct 1070 and the salivary duct opening (e.g., papilla 1060) can be accomplished by applying a proximal force on the sheath 1000 until the sheath 1000 is removed from the salivary duct 1070 and the salivary duct opening. Alternatively, the step of withdrawing the sheath 1000 from the salivary duct 1070 and salivary duct opening can be accomplished in combination with the step of withdrawing the basket 1100 from the salivary duct 1070, withdrawing the scope 1104 from the salivary duct 1070, and/or withdrawing the lithotripter 1106 from the salivary duct 1070.

While various catheter configurations, steps, alternative steps, and optional steps have been described above with respect to providing access to a salivary duct, these catheter configurations, steps, alternative steps, and optional steps can be included in, accomplished concurrently with, and/or accomplished in the alternative to, the methodologies, catheter configurations, steps, alternative steps, and/or optional steps described above with respect to the exemplary method of providing access 100 and the exemplary method of providing access 300.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A method of providing access to a salivary duct having a salivary duct opening, the method comprising the steps of:
    inserting a balloon catheter having a balloon catheter proximal end and a balloon catheter distal end into said salivary duct opening such that the balloon catheter distal end is disposed in said salivary duct, the balloon catheter comprising a sheath, an elongate tubular member, and a balloon disposed on the elongate tubular member and moveable between a deflated configuration and an inflated configuration, the sheath having a sheath distal end;
    navigating the balloon catheter distal end into said salivary duct such that a portion of the balloon is disposed within said salivary duct;
    passing a fluid into the balloon to move the balloon from the deflated configuration to the inflated configuration and to dilate said salivary duct opening to a dilated salivary duct opening;
    removing a portion, or the entirety, of the fluid from the balloon;
    advancing the sheath distally to pass the sheath distal end through the dilated salivary duct opening such that a portion of the sheath is disposed within said salivary duct; and
    withdrawing the elongate tubular member from said salivary duct.

2. The method of claim 1, wherein an initial step comprises inserting a wire guide having a wire guide proximal end and a wire guide distal end into said salivary duct opening such that the wire guide distal end is disposed in said salivary duct; and
    wherein another step comprises navigating the wire guide distal end towards a point of treatment within said salivary duct.

3. The method of claim 1, wherein the step of advancing the sheath distally to pass the sheath distal end through the dilated salivary duct opening such that a portion of the sheath is disposed within said salivary duct is accomplished while the balloon is in the inflated configuration.

4. The method of claim 1, wherein the balloon catheter further comprises a dilator;
    further comprising the step of advancing the dilator distally such that a portion of the dilator is disposed within said salivary duct;
    wherein the step of advancing the dilator distally such that a portion of the dilator is disposed within said salivary duct is accomplished while the balloon is in the inflated configuration.

5. The method of claim 1, further comprising the step of inserting one or more medical devices through the sheath, the one or more medical devices selected from the group consisting of probes, scopes, cutting tools, elongate tubular members, endoscopes, stents, suction devices, graspers, forceps, lithotripters, balloons, drills, lasers, and baskets.

6. The method of claim 5, further comprising the steps of:
    advancing the one or more medical devices towards a point of treatment;
    providing treatment using the one or more medical devices; and
    withdrawing the one or more medical devices from the sheath.

7. The method of claim 1, wherein the sheath has a first outside diameter and the balloon has a second outside diameter in the inflated configuration; and
    wherein the second outside diameter is greater than the first outside diameter.

8. The method of claim 1, wherein the elongate tubular member has an elongate tubular member proximal end and an elongate tubular member distal end and a marker disposed between the elongate tubular member proximal end and the elongate tubular member distal end, the marker positioned along the elongate tubular member at a location that is disposed from the elongate tubular member distal end a distance substantially equal to the length of the dilator and the length of the balloon.

9. A method of providing access to a salivary duct having a salivary duct opening, the method comprising the steps of:
    inserting a wire guide having a wire guide proximal end and a wire guide distal end into said salivary duct opening such that the wire guide distal end is disposed in said salivary duct;
    navigating the wire guide distal end towards a point of treatment within said salivary duct;
    advancing a balloon catheter having a balloon catheter proximal end and a balloon catheter distal end over the previously placed wire guide such that the balloon catheter distal end is disposed in said salivary duct, the balloon catheter comprising a sheath, a dilator, an elongate tubular member, and a balloon disposed on the elongate tubular member and moveable between a deflated configuration and an inflated configuration, the sheath having a sheath distal end;

navigating the balloon catheter distal end into said salivary duct such that a portion of the balloon is disposed within said salivary duct;

passing a fluid into the balloon to move the balloon from the deflated configuration to the inflated configuration and to dilate said salivary duct opening to a dilated salivary duct opening;

removing a portion, or the entirety, of the fluid from the balloon;

advancing the sheath distally to pass the sheath distal end through the dilated salivary duct opening such that a portion of the sheath is disposed within said salivary duct;

advancing the dilator distally such that a portion of the dilator is disposed within said salivary duct;

withdrawing the elongate tubular member from said salivary duct; and withdrawing the dilator from said salivary duct.

10. The method of claim 9, wherein the step of advancing the sheath distally to pass the sheath distal end through the dilated salivary duct opening such that a portion of the sheath is disposed within said salivary duct is accomplished while the balloon is in the inflated configuration.

11. The method of claim 9, wherein the step of advancing the dilator distally such that a portion of the dilator is disposed within said salivary duct is accomplished while the balloon is in the inflated configuration.

12. The method of claim 9, further comprising the step of inserting one or more medical devices through the sheath, the one or more devices selected from the group consisting of probes, scopes, cutting tools, elongate tubular members, endoscopes, stents, suction devices, graspers, forceps, lithotripters, balloons, drills, lasers, and baskets.

13. The method of claim 12, further comprising the steps of:

advancing the one or more medical devices towards a point of treatment;

providing treatment using the one or more medical devices; and withdrawing the one or more medical devices from the sheath.

14. The method of claim 9, wherein the sheath has a first outside diameter and the balloon has a second outside diameter in the inflated configuration; and wherein the second outside diameter is greater than the first outside diameter.

15. The method of claim 9, wherein the elongate tubular member has an elongate tubular member proximal end and an elongate tubular member distal end and a marker disposed between the elongate tubular member proximal end and the elongate tubular member distal end, the marker positioned along the elongate tubular member at a location that is disposed from the elongate tubular member distal end a distance substantially equal to the length of the dilator and the length of the balloon.

16. A method of providing access to a salivary duct having a salivary duct opening, the method comprising the steps of:

inserting a wire guide having a wire guide proximal end and a wire guide distal end into said salivary duct opening such that the wire guide distal end is disposed in said salivary duct;

navigating the wire guide distal end towards a point of treatment within said salivary duct;

advancing a balloon catheter having a balloon catheter proximal end and a balloon catheter distal end over the previously placed wire guide such that the balloon catheter distal end is disposed in said salivary duct, the balloon catheter comprising a sheath, a dilator, an elongate tubular member, and a balloon disposed on the elongate tubular member and moveable between a deflated configuration and an inflated configuration, the sheath having a sheath distal end;

navigating the balloon catheter distal end into said salivary duct such that a portion of the balloon is disposed within said salivary duct;

passing a fluid into the balloon to move the balloon from the deflated configuration to the inflated configuration and to dilate said salivary duct opening to a dilated salivary duct opening;

removing a portion, or the entirety, of the fluid from the balloon;

advancing the sheath distally to pass the sheath distal end through the dilated salivary duct opening such that a portion of the sheath is disposed within said salivary duct;

advancing the dilator distally such that a portion of the dilator is disposed within said salivary duct;

withdrawing the elongate tubular member from said salivary duct; and withdrawing the dilator from said salivary duct;

wherein the step of advancing the sheath distally to pass the sheath distal end through the dilated salivary duct opening such that a portion of the sheath is disposed within said salivary duct is accomplished while the balloon is in the inflated configuration.

17. The method of claim 16, wherein the step of advancing the dilator distally such that a portion of the dilator is disposed within said salivary duct is accomplished while the balloon is in the inflated configuration.

18. The method of claim 16, further comprising the step of inserting one or more medical devices through the sheath, the one or more devices selected from the group consisting of probes, scopes, cutting tools, elongate tubular members, endoscopes, stents, suction devices, graspers, forceps, lithotripters, balloons, drills, lasers, and baskets.

19. The method of claim 18, further comprising the steps of:

advancing the one or more medical devices towards a point of treatment;

providing treatment using the one or more medical devices; and withdrawing the one or more medical devices from the sheath.

20. The method of claim 16, wherein the sheath has a first outside diameter and the balloon has a second outside diameter in the inflated configuration; and wherein the second outside diameter is greater than the first outside diameter.

* * * * *